US009862737B2

(12) United States Patent
Pauls et al.

(10) Patent No.: US 9,862,737 B2
(45) Date of Patent: *Jan. 9, 2018

(54) SALTS, PRODRUGS AND POLYMORPHS OF FAB I INHIBITORS

(71) Applicant: Debiopharm International SA, Lausanne (CH)

(72) Inventors: Henry Pauls, Oakville (CA); Jailall Ramnauth, Brampton (CA)

(73) Assignee: Debiopharm International SA, Lausanne (CH)

( * ) Notice: Subject to any disclaimer, the term of this patent is extended or adjusted under 35 U.S.C. 154(b) by 206 days.

This patent is subject to a terminal disclaimer.

(21) Appl. No.: 14/075,470

(22) Filed: Nov. 8, 2013

(65) Prior Publication Data
US 2014/0309191 A1  Oct. 16, 2014

Related U.S. Application Data

(63) Continuation of application No. 13/570,747, filed on Aug. 9, 2012, now abandoned, which is a continuation of application No. 12/032,001, filed on Feb. 15, 2008, now Pat. No. 8,263,613.

(60) Provisional application No. 60/890,319, filed on Feb. 16, 2007.

(51) Int. Cl.
| C07D 471/04 | (2006.01) |
| C07F 9/22 | (2006.01) |
| A01N 43/90 | (2006.01) |
| A01N 57/16 | (2006.01) |
| A01N 57/32 | (2006.01) |
| C07F 9/145 | (2006.01) |

(52) U.S. Cl.
CPC .............. *C07F 9/222* (2013.01); *A01N 43/90* (2013.01); *A01N 57/16* (2013.01); *A01N 57/32* (2013.01); *C07D 471/04* (2013.01); *C07F 9/145* (2013.01)

(58) Field of Classification Search
CPC .................................................. C07D 471/04
See application file for complete search history.

(56) References Cited

U.S. PATENT DOCUMENTS

| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody |
| 6,288,239 B1 | 9/2001 | Hollingsworth et al. |
| 6,291,462 B1 | 9/2001 | Bartholomaeus et al. |
| 6,294,192 B1 | 9/2001 | Patel et al. |
| 6,303,572 B1 | 10/2001 | Rowe |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Cagle et al. |
| 6,399,629 B1 | 6/2002 | Chamberland et al. |
| 6,406,880 B1 | 6/2002 | Thornton |
| 6,423,341 B1 | 7/2002 | Yamaguchi |
| 6,423,741 B1 | 7/2002 | Khanuja et al. |
| 6,428,579 B1 | 8/2002 | Valentini |
| 6,432,444 B1 | 8/2002 | Fischetti et al. |
| 6,436,980 B1 | 8/2002 | Leger et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |

(Continued)

FOREIGN PATENT DOCUMENTS

| CA | 2444597 | 10/2002 |
| EP | 0407200 | 1/1991 |

(Continued)

OTHER PUBLICATIONS

Gould, "Salt Selection for Basic Drugs", International Journal of Pharmaceutics, 33, 1986, pp. 201-217.*
Abou-Gharbia et al., "Psychotropic Agents: Synthesis and Antipysychotic Activity of Substituted B-Carbolines," *J. Med. Chem.*, 30(6)1100-1115(1987).
Ahsan et al., "Reserpine Anlogues: Synthesis of B-Carboline Derivatives," *J. Chem.Soc.*, pp. 3928-3920(1963).
Database CA on STN, AN 7:66733, Rosenmund et al., "Chemistry of indole II . . .," *Chem Ber.*103(2): 496-509(1970).
Database CAOLD on STN, AN CA51:10524d, Hellman et al., "N-Mannich bases (VI) condensation . . .," *Direct Submission*(1953).
Database CAPLUS on STN, AN 1977:439214. Misztal et al., "Synthesis and pharmacologic properties of pyridoyl . . .," *Arch Immuno Ther Exp.*24(6):851-862(1976).
Database CAPLUS on STN, AN 1986:68547, Stuetz, et al., "Synthesis and Structure Activity . . .," *J. Med Chem.*, 29(1): 112-25 (1986).

(Continued)

Primary Examiner — Sahar Javanmard
(74) Attorney, Agent, or Firm — Goodwin Procter LLP

(57) ABSTRACT

In part, the present invention is directed to antibacterial compounds and salts thereof.

8 Claims, 20 Drawing Sheets

(56) References Cited

U.S. PATENT DOCUMENTS

| | | |
|---|---|---|
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw et al. |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,703,684 B2 | 3/2004 | Udrea et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | DeWolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 * | 5/2006 | Burgess ............ A61K 31/16 514/215 |
| 7,250,424 B2 | 7/2007 | Burgess et al. |
| 7,524,843 B2 | 4/2009 | Miller et al. |
| 7,557,125 B2 | 7/2009 | Miller et al. |
| 8,263,613 B2 | 9/2012 | Pauls et al. |
| 2003/0232850 A1 | 12/2003 | Miller et al. |
| 2004/0053814 A1 | 3/2004 | Brandt et al. |
| 2005/0004095 A1 | 1/2005 | Glinka et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |

FOREIGN PATENT DOCUMENTS

| | | |
|---|---|---|
| EP | 1000935 | 5/2000 |
| HU | 210679 | 7/1993 |
| HU | 0203122 | 1/2003 |
| WO | WO-93/04035 | 3/1993 |
| WO | WO-95/18619 | 7/1995 |
| WO | WO-96/00730 | 1/1996 |
| WO | WO-97/48696 | 12/1997 |
| WO | WO-98/57952 | 12/1998 |
| WO | WO-99/24406 | 5/1999 |
| WO | WO-00/27628 | 5/2000 |
| WO | WO-00/57933 | 10/2000 |
| WO | WO-01/26652 | 4/2001 |
| WO | WO-01/26654 | 4/2001 |
| WO | WO-01/27103 | 4/2001 |
| WO | WO-01/41573 | 6/2001 |
| WO | WO-01/48248 | 7/2001 |
| WO | WO-01/70172 | 9/2001 |
| WO | WO-02/10332 | 2/2002 |
| WO | WO-02/42273 | 5/2002 |
| WO | WO-02/48097 | 6/2002 |
| WO | WO-02/064572 | 8/2002 |
| WO | WO-03/086396 | 10/2003 |
| WO | WO-04/014869 | 2/2004 |
| WO | WO-04/52890 | 6/2004 |
| WO | WO-04/82586 | 9/2004 |
| WO | WO-07/053131 | 5/2007 |
| WO | WO-07/067416 | 6/2007 |
| WO | WO-08/009122 | 1/2008 |

OTHER PUBLICATIONS

Database CAPLUS on STN, AN 1991:428908, Fuse et al., "Preparation of cinnamamide derivatives . . .," EP407200A1 (1991).
Database CAPLUS on STN, AN 1999;325910 Aslanian , et al., "Preparation of phenylalkylimidazoles . . .," WO99/24406. (1999).
Database Crossfire Beilstein, 1966, Database accession No. 2819049, 2819050, XP002216033.
Himmer et al., "Synthesis and Antibacterial in Vitro Activity of Novel Analogues of Nematophin," *Bioorganic & Medicinal Chemistry Letters*, 8(15):2045-2050 (Aug. 1998).
Hungarian Search Report dated Dec. 31, 2003.
International Search Report dated Apr. 7, 2008 for PCT/CA2008/000300.
Jianxiong Li et al., "Synthesis and Antistaphylococcal Activity of Nematophin and Its Analogs," *Bioorganic & Medicinal Chemistry Letters*Oxford, GB, 7(10): 1349-1352, (May 20, 1977) XP004136332.
Karlowsky et al. "In Vitro activity of API-1252, a novel FabI inhibitor, against clinical isolates of *staphylococcus aureus and staphylococcus epidermidis*" Antimicrobial Agents and Chemotherapy, Apr. 2007, p. 1580-1581 (published on Jan. 12, 2007).
Miller et al., Discovery of Aminopyridine-Based Inhibitors of Bacterial Enoyl-ACP Reductase (FABI): *J. Med. Chem.*, 2002, vol. 45, pp. 3246-3256.
Misztal et al., "Synthesis and Pharmacologic Properties of Pyridol Derivatives of 3-Methylaminoindole 2-Methyltryptamine and lsostryptamine," *Archivum Immnologiae et Therapiae Exserimentalis*, 24(6): 851-852 (1976).
Pachter et al., "The Chemistry of Hortiamine and 6-Methoxyhetsinine," *J. Amer. Chem.*, 83:635-642 (1961).
Rehse et al., "Dopaminanaloge 1,2,3,4-Tetrahydro-B-Carboline," *Arch. Pharm.*, 311(1): 11-18.
Shoji et al., Two Novel Alkaloids from Evodia Rutaecarpa, *J. Natural Products*, 52(5):1160-1162.
Stutz et al. "Synthesis and Structure-Activity Relationships of Naftifine-Related Allylamine Antimycotics," *Journal of Medicinal Chemistry*, 1986, vol. 29, No. 1, 112-125.
Bergler, Helmut, et al., "Protein EnvM is the NADH-dependent Enoyl-ACP Reductase (FabI) of Escherichia Coli," *J. Biological Chemistry*, vol. 269, No. 8, Feb. 25, 1994, pp. 5493-5496.
Claus et al., *Monatsh. Chem.*97:271-279 (1966).
Grassberger, Maximilian, et al., "Preparation and Antibacterial Activities of New 1,2,3-Diazaborine Derivatives and Analogues," *J. Med. Chemistry*, 1984, 27, 947-953.

(56) References Cited

OTHER PUBLICATIONS

Heath, Richard J., et al., "A Triclosan-Resistant Bacterial Enzyme," *Nature*, vol. 406, Jul. 13, 2000, p. 145-146.
Heath, Richard J., et al., "Regulation of Fatty Acid Elongation and Initiation by Acyl-Acyl Carrier Protein in Escherichia Coli," *J. Biological Chemistry*, vol. 271, No. 4, Jan. 26, 1996, pp. 1833-1836.
Heck, Richard F., *Organic Reactions*, 1982, 27, pp. 345-390.
International Search Report dated Oct. 4, 2000 for PCT/US2000/15154.
International Search Report dated Jan. 25, 2001 for PCT/US2000/27844.
International Search Report dated Jan. 29, 2001 for PCT/US2000/27591.
International Search Report dated Feb. 22, 2001 for PCT/US2000/27619.
International Search Report dated Apr. 21, 2004 for PCT/US2003/38706.
International Search Report dated Oct. 13, 2004 for PCT/IB2004/001261.
International Search Report dated Apr. 20, 2005 for PCT/US2002/10332.
International Search Report dated Jun. 14, 2007 for PCT/US2005/019805.
International Search Report dated Sep. 12, 2007 for PCT/US2006/045903.
International Search Report dated Oct. 26, 2007 for PCT/CA2007/001277.
Jossang-Yanagida, Akino, et al., "Tetrahydropyridoazepines and Tetrahydropyridoazepinones from the Corresponding Dihydroquinolones," *J. Heterocyclic Chemistry*, vol. 15, pp. 249-251.
Levy, Colin W., et al., "Molecular Basis of Triclosan Activity," *Nature*, vol. 398, Apr. 1, 1999, pp. 383-384.
McMurray, Laura M., et al., "Triclosan Targets Lipid Synthesis," *Nature*, vol. 394, Aug. 4, 1998, pp. 531-532.
Patent Abstract of Japan vol. 2000, No. 2, Feb. 29, 2000, JP 11-302173.
Payne et al., *Drug Discovery Today*, 2008 pp. 537-541.
Seefeld et al., "Indole Naphthyridinones as Inhibitors of Bacterial Enoyl-ACP Reductases FabI and FabK" *J. Med. Chem.* 46:1627-1635 (2003).
Sladowska et al. "Synthesis and properties of amides of 1-benzyl-3-methyl and 1-butyl-3-phenyl-7methyl-4-oxo-2-thioxo (2,4-dioxo)-1,2,3,4-tetrahydropyrido-[2,3-d]pyrimidine-6-carboxylic acids" *Farmaco Edizione Scientifica* 1986 41:954-963.
Turnowsky, Friederike, et al., "envM Genes of Salmonella Typhimurium and Escherichia Coli," *J. Bacteriology*, vol. 171, No. 12, 12/89, pp. 6555-6565.
Ward, Walter H.J., et al., "Kinetic and Structural Characteristics of the Inhibition of Enoyl (Acyl Carrier Protein) Reductase by Triclosan," *Biochemistry*, 1999, vol. 38, No. 38, pp. 12514-12525.
Gould, "Salt Selection for Basic Drugs," *International Journal of Pharmaceutics*, vol. 33, (1986) pp. 201-217.

* cited by examiner

SALTS, PRODRUGS AND POLYMORPHS OF FAB I INHIBITORS

This application is a continuation application of U.S. Ser. No. 13/570,747, filed Aug. 9, 2012, which is a continuation application of U.S. Ser. No. 12/032,001, filed Feb. 15, 2008, now U.S. Pat. No. 8,263,613, which claims priority to U.S. Ser. No. 60/890,319, filed Feb. 16, 2007, each of which is hereby incorporated by reference in its entirety.

INTRODUCTION

Infections caused by or related to bacteria are a major cause of human illness worldwide, and the frequency of resistance to standard antibiotics has risen dramatically over the last decade. Hence, there exists an unmet medical need and demand for new agents acting against bacterial targets.

Examples of potential bacterial targets are those enzymes involved in fatty acid biosynthesis. While the overall pathway of saturated fatty acid biosynthesis is similar in all organisms, the fatty acid synthase (FAS) systems vary considerably with respect to their structural organization. It is believed that vertebrates and yeast possess a FAS in which all the enzymatic activities are encoded on one or two polypeptide chains, respectively, and the acyl carrier protein (ACP) is an integral part of the complex. In contrast, in bacterial FAS, it is known that each of the reactions is catalyzed by a distinct, mono-functional enzyme and the ACP is a discrete protein. Therefore, it may be possible to achieve selective inhibition of the bacterial system by appropriate agents.

One such potential bacterial target is the FabI protein. FabI (previously designated EnvM) is believed to function as an enoyl-ACP reductase in the final step of the four reactions involved in each cycle of bacterial fatty acid biosynthesis. It is believed that in this pathway, the first step is catalyzed by β-ketoacyl-ACP synthase, which condenses malonyl-ACP with acetyl-CoA (FabH, synthase III). It is believed that in subsequent rounds, malonyl-ACP is condensed with the growing-chain acyl-ACP (FabB and FabF, synthases I and II, respectively). The second step in the elongation cycle is thought to be ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP. Finally, in step four, trans-2-enoyl-ACP is converted to acyl-ACP by an NADH (or NADPH)-dependent enoyl-ACP reductase (Fab I). Further rounds of this cycle, adding two carbon atoms per cycle, would eventually lead to palmitoyl-ACP (16C), where upon the cycle is stopped largely due to feedback inhibition of Fab I by palmitoyl-ACP. Thus, Fab I is believed to be a major biosynthetic enzyme and is a key regulatory point in the overall synthetic pathway of bacterial fatty acid biosynthesis.

In some bacteria the final step of fatty acid biosynthesis is catalyzed by Fab I only, in others by FabK, an NADH and FMN dependent reductase, still others utilize both FabI and FabK. The present invention provides, in part, compounds and compositions with FabI inhibiting properties.

SUMMARY

In part, the present invention is directed towards salts and polymorphs of compounds with FabI inhibiting properties as well as other enzymes. Other uses for the subject compounds and compositions will be readily discernable to those of skill in the art.

Also disclosed herein are methods and/or synthetic routes for large scale preparation of (E)-N-methyl-N-((3-methylbenzofuran-2-yl)methyl)-3-(7-oxo-5,6,7,8-tetrahydro-1,8-naphthyridin-3-yl)acrylamide and its toluene sulfonic acid salt forms.

In an embodiment, this disclosure provides for a composition that may be substantially free of palladium and comprises (E)-N-methyl-N-((3-methylbenzofuran-2-yl)methyl)-3-(7-oxo-5,6,7,8-tetrahydro-1,8-naphthyridin-3-yl) acrylamide and/or its salts, hydrates, and prodrug forms, for example, toluene sulfonic acid salt forms.

Figure 15:
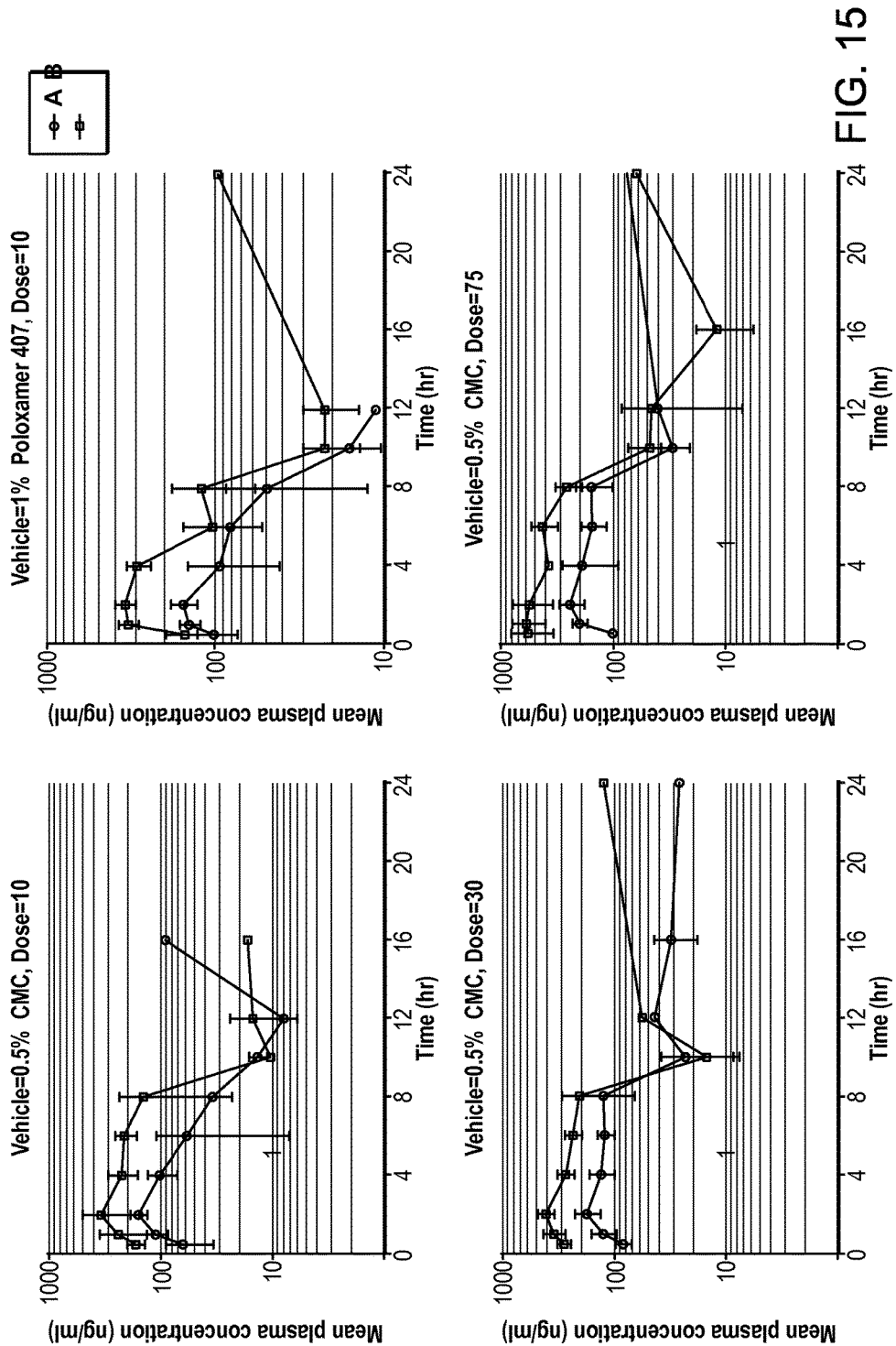

FIG. 15 depicts plasma time concentrations of the free base and the tosylate monohydrate salt of Compound A in a rat model.

DETAILED DESCRIPTION

Introduction

The present disclosure is directed in part towards novel compounds and/or compositions that inhibit bacterial enzymes, and methods of making and using the same. In part, the disclosure is directed to salts, prodrugs, hydrates, and/or polymorphs of (E)-N-methyl-N-((3-methylbenzo-furan-2-yl)methyl)-3-(7-oxo-5,6,7,8-tetrahydro-1,8-naph-thyridin-3-yl)acrylamide, referred to as "compound A" throughout this disclosure.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "including" is used to mean "including but not limited to". "Including" and "including but not limited to" are used interchangeably.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria and plants.

The term "enzyme inhibitor" refers to any compound that prevents an enzyme from effectively carrying out its respective biochemical roles. Therefore a "FabI inhibitor" is any compound that inhibits FabI from carrying out its biochemical role. The amount of inhibition of the enzyme by any such compound will vary and is described herein and elsewhere.

The term "antibiotic agent" shall mean any drug that is useful in treating, preventing, or otherwise reducing the severity of any bacterial disorder, or any complications thereof, including any of the conditions, disease, or complications arising therefrom and/or described herein. Antibiotic agents include, for example, cephalosporins, quinolones and fluoroquinolones, penicillins, penicillins and beta lactamase inhibitors, carbepenems, monobactams, macrolides and lin-cosamines, glycopeptides, rifampin, oxazolidonones, tetracyclines, aminoglycosides, streptogramins, sulfonamides, and the like. Other general categories of antibiotic agents which may be part of a subject composition include those agents known to those of skill in the art as antibiotics and that qualify as (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. §355(a) ("regulatory approved drug"); any agent that is or was subject to a human drug application under 21 U.S.C. §379(g) ("human drug"). (All references to statutory code for this definition refer to such code as of the original filing date of this provisional application.) Other antibiotic agents are disclosed herein, and are known to those of skill in the art. In certain embodiments, the term "antibiotic agent" does not include an agent that is a FabI inhibitor, so that the combinations of the present invention in certain instances will include one agent that is a FabI inhibitor and another agent that is not.

The term "illness" as used herein refers to any illness caused by or related to infection by an organism.

The term "bacterial illness" as used herein refers to any illness caused by or related to infection by bacteria.

The term "cis" is art-recognized and refers to the arrangement of two atoms or groups around a double bond such that the atoms or groups are on the same side of the double bond. Cis configurations are often labeled as (Z) configurations.

The term "substantially the same" when used to describe X-ray powder diffraction patterns, is meant to include patterns in which peaks are within a standard deviation of ±0.2 2θ.

The term "trans" is art-recognized and refers to the arrangement of two atoms or groups around a double bond such that the atoms or groups are on the opposite sides of a double bond. Trans configurations are often labeled as (E) configurations.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Antibiotic agents and Fab I/Fab K inhibitors are examples of therapeutic agents.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "$K_i$" is art-recognized and refers to the dissociation constant of the enzyme-inhibitor complex.

The term "antimicrobial" is art-recognized and refers to the ability of the compounds of the present invention to prevent, inhibit or destroy the growth of microbes such as bacteria, fungi, protozoa and viruses.

The term "antibacterial" is art-recognized and refers to the ability of the compounds of the present invention to prevent, inhibit or destroy the growth of microbes of bacteria.

The term "microbe" is art-recognized and refers to a microscopic organism. In certain embodiments the term microbe is applied to bacteria. In other embodiments the term refers to pathogenic forms of a microscopic organism.

The term "prodrug" is art-recognized and is intended to encompass compounds which, under physiological conditions, are converted into the antibacterial agents of the present invention. A common method for making a prodrug is to select moieties which are hydrolyzed under physiological conditions to provide the desired compound. In other embodiments, the prodrug is converted by an enzymatic activity of the host animal or the target bacteria.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on 560 of "*Advanced Inorganic Chemistry*" by Cotton and Wilkinson.

The definition of each expression, e.g. alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate, p-toluenesulfonate, methanesulfonate, and nonafluorobutanesulfonate functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67$^{th}$ Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The definition of each expression, e.g. lower alkyl, m, n, p and the like, when it occurs more than once in any structure, is intended to be independent of its definition elsewhere in the same structure.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compositions described herein include compositions which otherwise correspond thereto, and which have the same general properties thereof (such as other compositions comprising FabI/Fab K inhibitors or salts and/or hydrates and/or prodrugs and/or polymorphs of Compound A), wherein one or more simple variations of substituents or components are made which do not adversely affect the characteristics of the compositions of interest. In general, the components of the compositions of the present invention may be prepared by the methods illustrated in the general reaction schema and written procedures as, for example, described below, or by modifications thereof, using readily available starting materials, reagents and conventional synthesis procedures. In these reactions, it is also possible to make use of variants which are in themselves known, but are not mentioned here.

FabI Inhibitors

The FabI inhibitor compounds of the present invention include those depicted by formula I:

Formula I

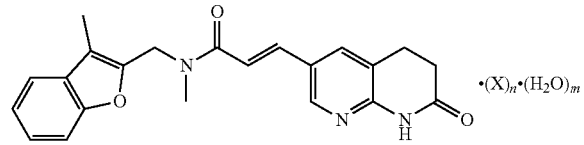

wherein n is a fractional or whole number between about 0 and about 1.5 inclusive; m is a integer or whole (e.g. fractional) number between about 0 and about 3 inclusive; X is selected from the group consisting of $H_2SO_4$, $HSO_3R'$, $HSO_3Ar$, $H_3PO_4$, $HCl$, $HBr$, $CF_3CO_2H$, and $Cl_3CO_2H$; R' is alkyl; and Ar is aryl. Ar may be, for example, p-toluene or benzene.

In cases wherein such inhibitors may have one or more chiral centers, unless specified, the present invention comprises each unique racemic compound, as well as each unique nonracemic compound.

In cases in which the inhibitors have unsaturated carbon-carbon double bonds, both the cis (Z) and trans (E) isomers are within the scope of this invention. In cases wherein inhibitors may exist in tautomeric forms, such as keto-enol tautomers, such as

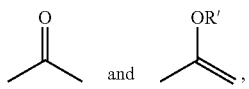

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

In some embodiments, n may be a fractional or whole number between about 0 and about 1.5 inclusive, for example n may be about 1. In other embodiments, m maybe a fractional or whole number between about 0 and about 3, inclusive, for example m may be 0, 1, 2 or 3.

For example, compound A may be in a free base, anhydrous form (e.g. n is 0 and m is 0 in formula I). Alternatively, hydrates of compound A are also contemplated herein (m>0), for example, a hydrate of compound A may be a monohydrate, (e.g. n=0 and m is 1).

Hydrates are also provided when n is about 1 or more. For example, the p-toluenesulfonic salt of (E)-N-methyl-N-((3-methylbenzofuran-2-yl)methyl)-3-(7-oxo-5,6,7,8-tetrahydro-1,8-naphthyridin-3-yl)acrylamide may be provided in anhydrous (m=0) or monohydrate (m=1) form.

Polymorphs of compound A, and salts, hydrates and prodrugs are also contemplated herein. Such polymorphs can be produced by e.g. using crystallization conditions to isolate a free-base and salt forms and/or by ball-milling such forms.

Also included in the antibiotic compounds of the present invention are prodrugs of the FabI inhibitors. The FabI inhibitor compounds of the present invention include those depicted by A compound of formula II:

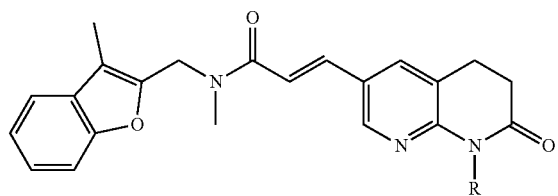

II wherein R is a labile modifying group that is capable of releasing the compound (E)-N-methyl-N-((3-methylbenzofuran-2-yl)methyl)-3-(7-oxo-5,6,7,8-tetrahydro-1,8-naphthyridin-3-yl)acrylamide in vivo. The pharmaceutically acceptable salts of Formula II are also contemplated. In some embodiments R may be for example selected from the group consisting of —CO$_2$R', —CH$_2$OC(O)R', —PO$_3$Ca, —PO$_3$Mg, —PO$_3$Na$_2$, and —PO$_3$K$_2$, where R' is alkyl.

Compounds disclosed herein include: (E)-N-methyl-N-((3-methylbenzofuran-2-yl)methyl)-3-(7-oxo-5,6,7,8-tetrahydro-1,8-naphthyridin-3-yl)acrylamide hydrochloride; (E)-N-methyl-N-((3-methylbenzofuran-2-yl)methyl)-3-(7-oxo-5,6,7,8-tetrahydro-1,8-naphthyridin-3-yl)acrylamide hydrobromide; (E)-N-methyl-N-((3-methylbenzofuran-2-yl)methyl)-3-(7-oxo-5,6,7,8-tetrahydro-1,8-naphthyridin-3-yl)acrylamide sulfate; (E)-N-methyl-N-((3-methylbenzofuran-2-yl)methyl)-3-(7-oxo-5,6,7,8-tetrahydro-1,8-naphthyridin-3-yl)acrylamide methane sulfonate; (E)-N-methyl-N-((3-methylbenzofuran-2-yl)methyl)-3-(7-oxo-5,6,7,8-tetrahydro-1,8-naphthyridin-3-yl)acrylamide ethane sulfonate; (E)-N-methyl-N-((3-methylbenzofuran-2-yl)methyl)-3-(7-oxo-5,6,7,8-tetrahydro-1,8-naphthyridin-3-yl)acrylamide 2-hydroxyethanesulfonate; (E)-N-methyl-N-((3-methylbenzofuran-2-yl)methyl)-3-(7-oxo-5,6,7,8-tetrahydro-1,8-naphthyridin-3-yl)acrylamide 4-methylbenzenesulfonate; (E)-N-methyl-N-((3-methylbenzofuran-2-yl)methyl)-3-(7-oxo-5,6,7,8-tetrahydro-1,8-naphthyridin-3-yl)acrylamide 4-methylbenzenesulfonate monohydrate; (E)-N-methyl-N-((3-methylbenzofuran-2-yl)methyl)-3-(7-oxo-5,6,7,8-tetrahydro-1,8-naphthyridin-3-yl)acrylamide benzenesulfonate; (E)-N-methyl-N-((3-methylbenzofuran-2-yl)methyl)-3-(7-oxo-5,6,7,8-tetrahydro-1,8-naphthyridin-3-yl)acrylamide phosphate; (E)-N-methyl-N-((3-methylbenzofuran-2-yl)methyl)-3-(7-oxo-5,6,7,8-tetrahydro-1,8-naphthyridin-3-yl)acrylamide trifluoroacetate; (E)-N-methyl-N-((3-methylbenzofuran-2-yl)methyl)-3-(7-oxo-5,6,7,8-tetrahydro-1,8-naphthyridin-3-yl)acrylamide trichloroacetate; (E)-6-(3-(methyl((3-methylbenzofuran-2-yl)methyl)amino)-3-oxoprop-1-enyl)-2-oxo-3,4-dihydro-1,8-naphthyridin-1(2H)-ylphosphonic acid; Calcium (E)-6-(3-(methyl((3-methylbenzofuran-2-yl)methyl)amino)-3-oxoprop-1-enyl)-2-oxo-3,4-dihydro-1,8-naphthyridin-1(2H)-ylphosphonate; Magnesium (E)-6-(3-(methyl((3-methylbenzofuran-2-yl)methyl)amino)-3-oxoprop-1-enyl)-2-oxo-3,4-dihydro-1,8-naphthyridin-1(2H)-ylphosphonate; Disodium (E)-6-(3-(methyl((3-methylbenzofuran-2-yl)methyl)amino)-3-oxoprop-1-enyl)-2-oxo-3,4-dihydro-1,8-naphthyridin-1(2H)-ylphosphonate; and Dipotassium (E)-6-(3-(methyl((3-methylbenzofuran-2-yl)methyl)amino)-3-oxoprop-1-enyl)-2-oxo-3,4-dihydro-1,8-naphthyridin-1(2H)-ylphosphonate; (Z)—N-methyl-N-((3-methylbenzofuran-2-yl)methyl)-3-(7-oxo-5,6,7,8-tetrahydro-1,8-naphthyridin-3-yl)acrylamide and rotamers thereof.

Cis-trans amide rotamers of compound A and salts, hydrates or prodrugs thereof are also contemplated. For example, at ambient temperature, an amide bond may not have any free rotation. At an elevated temperature, e.g. about 70 to about 100° C., an amide molecule may establish trans and cis rotameric equilibrium. At these temperature, free rotation around the amide can occur, and $^1$H NMR spectrum may sharpen. Exemplary cisoid and transoid rotamers are shown by the formula III and IV:

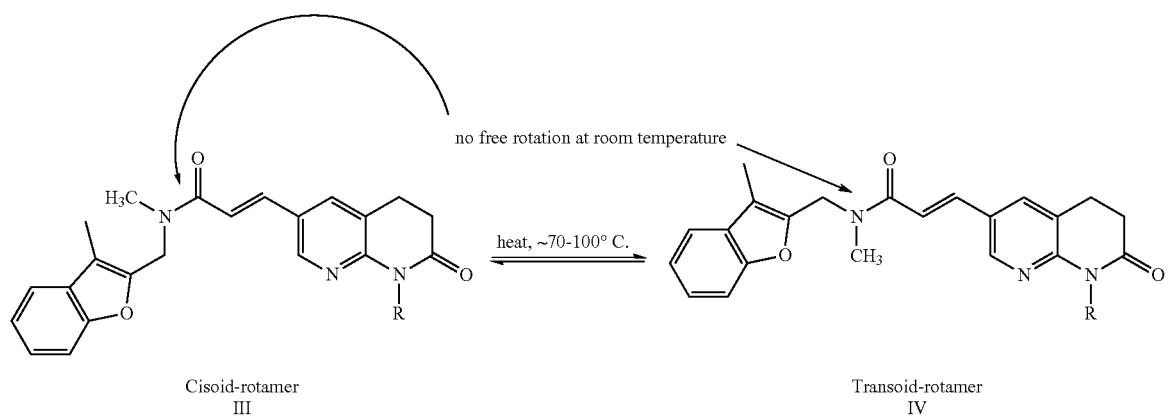

Cisoid-rotamer
III

Transoid-rotamer
IV

Cis-isomers of compound A or salts, hydrates, or prodrugs thereof is also contemplated, for example, as shown in formula V. Pharmaceutical salts, hydrates or prodrugs of cis-isomers are also contemplated.

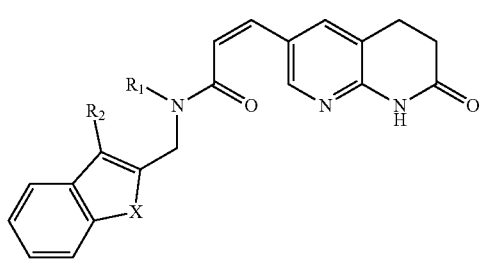

V $R_1$ may be H or alkyl, e.g., methyl, $R_2$ may be H or alkyl, and X may be O or S.

Reaction Methods

Methods I to III are directed to chemistry involved in the synthesis of salts and/or hydrates of compound A. One of skill in the art would understand that the disclosed salts can be made in a variety of ways that may differ from the exemplary schemes described below. Acid addition salts of the compounds of formula I can be prepared in a standard manner in a suitable solvent from the parent compound and an excess of an acid, such as hydrochloric, hydrobromic, hydrofluoric, sulfuric, phosphoric, acetic, trifluoroacetic, maleic, citric, succinic or methanesulfonic. Certain of the compounds form inner salts or zwitterions which may be acceptable. Cationic salts may be prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are some non-limiting examples of cations present.

Method I

General Method of Salt Formation I: Combinatorial Screen

A matrix of 10 acids (maleic acid, p-toluenesulfonic acid, benzenesulfonic acid, methansulfonic acid, trichloroacetic acid, trifluoroacetic acid, hydrobromic acid, hydrochloric acid, sulfuric acid, and phosphoric acid) and six solvents (dioxane, THF, DMF, AcOH, DCM, DMA) can be laid out in a e.g. 96 well plate with the counter ions occupying the first 10 columns and the solvents the first six rows. Each well can be charged with e.g. $4.66 \times 10^{-6}$ mol of the (E)-N-methyl-N-((3-methylbenzofuran-2-yl)methyl)-3-(7-oxo-5,6,7,8-tetrahydro-1,8-naphthyridin-3-yl)acrylamide by combinatorially dispensing 500 μL of a 0.009 molar stock solution of compound A dissolved in solvent, for example, dichloromethane (DCM). The content of each well can then be concentrated to dryness under a slow stream of nitrogen using a 96 well plate nitrogen manifold.

The residues can be dissolve, for example, in 500 μL of e.g. 6 solvents (dioxane, THF, DMF, AcOH, DCM, DMA). An extra 250 μL can be added to the wells for dioxane and THF. The plate is placed in a heated block at 55° C. on top of an orbital shaker and shaken for 10 minutes to ensure dissolution. Each well is then charged with 39 μL of a 0.126 M solution of the acid in dioxane corresponding to 1.05 equivalents of each of the 10 acids. The plate is then placed back onto the orbital shaker and cooled to room temperature at a rate of 20° C./hour, after 3 hours the solvents were removed under a stream of nitrogen.

Determination of crystallinity can be performed on solid-containing wells by dispersing the solids in mineral oil and using a polarized light microscope at 100× and 400×. Samples which contain particles with distinct birefringence and extinction positions are typically identified as crystalline. Those which have particles that exhibit birefringence and extinction positions but also had a significant amount of particles which were not observed to reflect light can be typically described as partially crystalline. Amorphous solids are typically those which do not have significant amount of particles that reflected polarized light while deliquescent material becomes liquid-like or softened during analysis.

Table 1 summarizes representative solvents and amounts used for the generation of HBr, sulfuric acid, methane sulfonic acid (MsOH), benzene sulfonic acid and p-toluene sulfonic acid salts of compound A but may be applied to any of the combinations described herein.

TABLE 1

| Compound A amount (mg) | Solvent | Amount (mL) | Acid | Heptane Amount (mL) | Recovery (mg) |
|---|---|---|---|---|---|
| 19 | THF | 8 | HBr | 3 | 0.007 |
| 20 | DCM | 4 | HBr | 3 | 0.016 |
| 19 | THF | 8 | sulfuric | 3 | 0.004 |

TABLE 1-continued

| Compound A amount (mg) | Solvent | Amount (mL) | Acid | Heptane Amount (mL) | Recovery (mg) |
|---|---|---|---|---|---|
| 19 | THF | 8 | MsOH | 5 | 0.015 |
| 20 | DCM | 4 | MsOH | 2 | 0.019 |
| 20 | THF | 8 | benzenesulfonic | 4 | 0.007 |
| 20 | DCM | 5 | benzenesulfonic | 3 | 0.015 |
| 20 | THF | 8 | p-toluenesulfonic | 4 | 0.004 |
| 20 | DCM | 5 | p-toluenesulfonic | 3 | 0.016 |

Method II
General Method of Salt Formation II: Intermediate Scale
Variant A

This method employs combinations of counter-ion and solvent. Vials were charged with between 19-21 mg of (E)-N-methyl-N-((3-methylbenzofuran-2-yl)methyl)-3-(7-oxo-5,6,7,8-tetrahydro-1,8-naphthyridin-3-yl)acrylamide and are followed by one of the following solvents: DCM 2 mL, THF 10 mL, AcOH 4.5 mL, and DMA 3-4 mL. These vials are heated (DCM 32° C., THF 58° C., AcOH and DMA 90° C.) with stirring to ensure dissolution. Each vial is then charged with between 425-465 µL of a 0.126 M solution of the acid in dioxane corresponding to 1.05 equivalents of each of the acids.

The temperature is held at the dissolution temperature for 10 minutes and is then ramped down to room temperature at a rate of 20° C./hour. Typically, upon reaching room temperature the vials do not show any precipitation at this stage. The vials are allowed to evaporate to induce precipitation. Upon losing about one quarter of the volume the THF examples typically start to precipitate. The solids are then generally collected by filtration. In some cases the (eg. some DCM examples) most of the volume of solvent can evaporate before precipitation occurs and can not be filtered. In other situations, the vial contents may have to be concentrated before crystallization occurs. All solid products can be analyzed directly by XRPD and DSC.

Variant B

In a variant of general method II vials are charged with between 19-21 mg of the API were treated with one of the above solvents (i.e. DCM or THF). These vials are heated (DCM 32° C., THF 58° C.) with stirring to ensure dissolution. Each vial is then charged with between 425 to 465 µL of a 0.126 M solution of the acid in dioxane corresponding to 1.05 equivalents of each acid. The temperature is held (DCM 32° C., THF 58° C.) for 10 minutes before the introduction of an anti-solvent such as heptane. Heptane can be added until the solution became turbid, 3 mL for THF experiment and 1.5 mL for DCM experiment. After addition the vials are allowed to cool to room temperate at a rate of 20° C./hour. Precipitation typically occurs during the cooling phase and the solids can be collected by filtration and dried in vacuo at 50° C. and 30 inches of Hg.

Method III
General Method of Salt Formation III: Scale-Up

Scale-up reactions can be carried out on, for example, 1 gram of material. Table 2 summarizes typical amounts of solvents and reagents used for exemplary scale up reactions although variations in solvent and Compound A amount can be employed.

TABLE 2

| Compound A amnt (g) | Solvent | solvent amnt (mL) | Acid | Amount of 1M solution (mL) | Anti-solvent amnt (mL) | Yield % |
|---|---|---|---|---|---|---|
| 1.000 | THF | 350 | p-TSA | 2.8 | 144 | 77.8 |
| 1.016 | THF | 350 | sulfuric | 2.82 | 34 | 83.7 |
| 1.000 | DCM | 200 | MsOH | 2.8 | 150 | 84.4 |

Compound A is dissolved in the appropriate amount of solvent with heating and stirring. To this is added the acid solution at for example 1 M concentration, and the delivery solvent is matched with the reaction solvent. After stirring for 5 minutes the anti-solvent (typically a hydrocarbon e.g. heptane) is added. Enough anti-solvent is added to form a turbid solution that typically clears up after a few seconds. The reactions are heated back to the reaction temperature if any cooling occurred during the anti-solvent addition. The temperatures are then ramped down to room temperature at a rate of about 20° C./hour. The solids are then collected by filtration and dried in vacuo (55° C. and 30 inches of Hg).

Method IV
Phosphonate Prodrugs

Processes for the preparation of Compound A phosphonic acid and its salts are outlined in Scheme I. For example, Compound A is reacted with base and a source of di-(arylmethyl)-phosphoro radical such as, for example, dibenzylphosphoro chloride or tetrabenzylpyrophosphate to obtain the diarylmethyl phosphonate, attached at the naphthyridinyl 8-nitrogen of Compound A as shown in Scheme I. Arylmethyl groups attached to the phosphate, such as benzyl, can generally be removed by hydrogenolysis conditions, such as hydrogen gas with palladium on carbon catalyst, in the presence of a metallic base, such as potassium carbonate, or an amine base, such as triethyl amine, to yield the corresponding phosphonate salts.

Alternatively, Compound A can be reacted with, for example, a base and a source of diaryl phosphate radical such as diphenylphosphoro chloride to obtain the diaryl phosphonate of Compound A attached at the naphthyridinyl 8-nitrogen of Compound A as shown in Scheme I. Aryl groups attached to the phosphate, such as phenyl, are generally reacted under basic conditions, such as sodium hydroxide to yield the corresponding disodium salt of the depicted phosphonate.

When R is a small alkyl group (e.g. 1-4 carbons) trimethyl silyl iodide (TMSiI), followed by an aqueous quench may be used to generate the phosphonate of Compound A.

The phosphonate of Compound A may also be formed by reacting Compound A with phosphoric anhydride under elevated temperature and using a subsequent treatment with moist organic solvent, such as for example, ether.

The number of counter ions, n, in the phosphonate product may be dependent on the charge resident on the counter ion, M+. By way of illustration for a calcium salt ($Ca^{2+}$) one counter ion would be found. Alternatively for a tertiary amine counter ion such as triethylamine ($Et_3HN^+$) or a monovalent metal such as sodium ($Na^+$) or potassium ($K^+$), two counter ions are required.

Scheme II

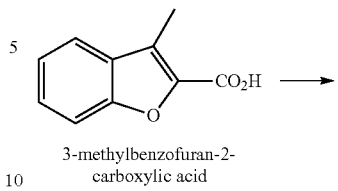

3-methylbenzofuran-2-carboxylic acid

Scheme I

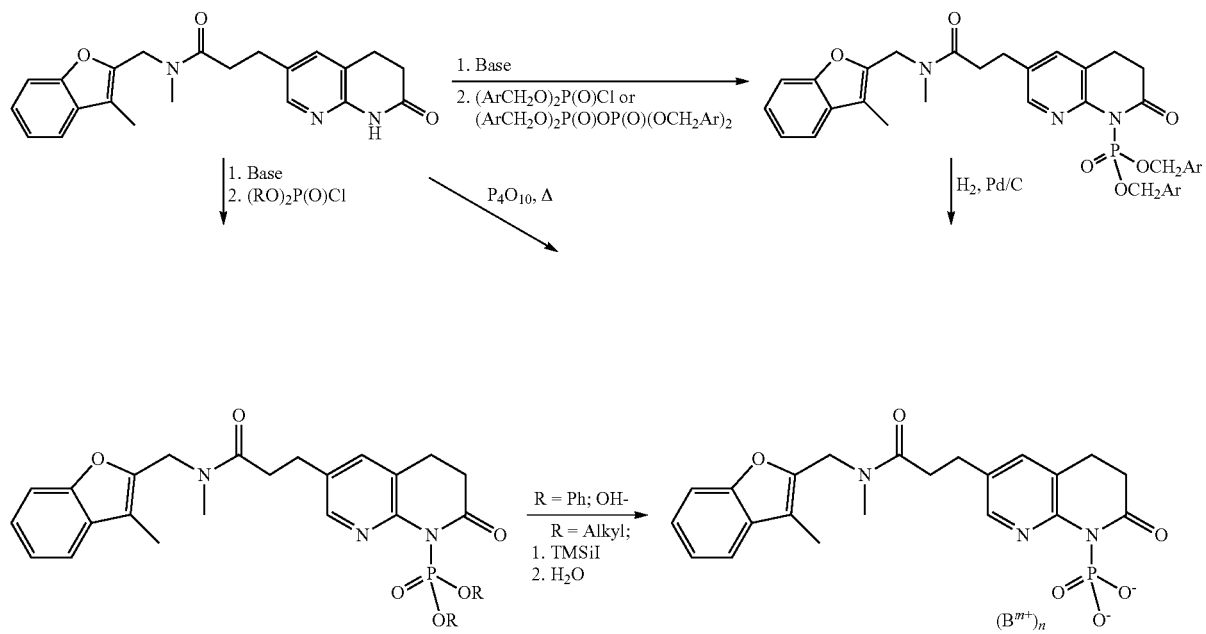

Method V:

Large scale preparation of (E)-N-methyl-N-((3-methyl-benzofuran-2-yl)methyl)-3-(7-oxo-5,6,7,8-tetrahydro-1,8-naphthyridin-3-yl)acrylamide and its toluene sulfonic acid salt forms.

Processes for the preparation of Compound A and its salts suitable for large scale processing are outlined in Scheme II. Exemplification of such large scale processes are provided in the below Examples 10-11. The large scale processes disclosed herein result in a final product that may be substantially free of palladium. A composition, comprising (E)-N-methyl-N-((3-methylbenzofuran-2-yl)methyl)-3-(7-oxo-5,6,7,8-tetrahydro-1,8-naphthyridin-3-yl)acrylamide and/or its salts, hydrates, and/or prodrug forms is contemplated that is substantially free of palladium, for example, has less than about 50 ppm, less than about 30 ppm, less than about 20 ppm, less than about 10 ppm of palladium. For example, such a composition may have about 0.01 to about 50 ppm of palladium, about 0.01 to about 20 ppm, about 0.01 to about 10 ppm of palladium. Also contemplated herein are compositions comprising less than about 100 ppm of heavy metals, e.g. about 0.01 ppm to about 100 pm of heavy metals.

-continued

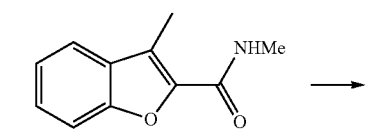

N, 3-dimethylbenzofuran-2-carboxamide

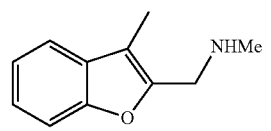

N-methyl-1-(3-methylbenzofuran-2-yl)methanamine

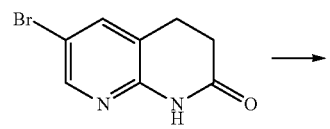

6-bromo-3,4-dihydro-1,8-naphthyridin-2(1H)-one

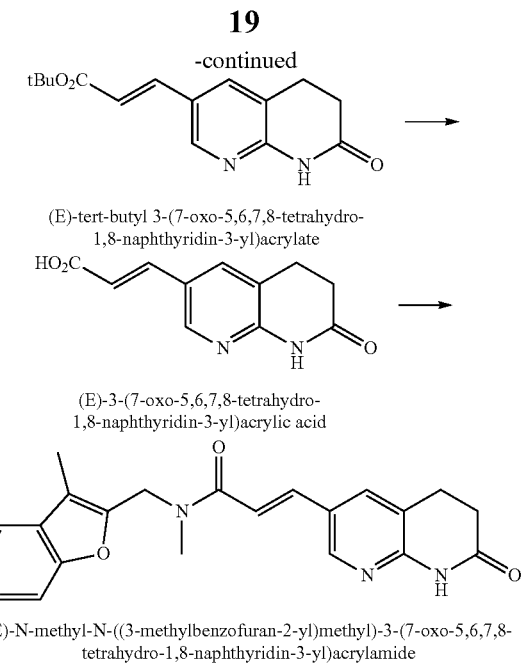

(E)-tert-butyl 3-(7-oxo-5,6,7,8-tetrahydro-1,8-naphthyridin-3-yl)acrylate (E)-3-(7-oxo-5,6,7,8-tetrahydro-1,8-naphthyridin-3-yl)acrylic acid (E)-N-methyl-N-((3-methylbenzofuran-2-yl)methyl)-3-(7-oxo-5,6,7,8-tetrahydro-1,8-naphthyridin-3-yl)acrylamide The large scale processes disclosed herein (e.g. processes for making e.g about 0.5 kg or more of material include a large scale process for preparing substantially palladium free (E)-N-methyl-N-((3-methylbenzofuran-2-yl)methyl)-3-(7-oxo-5,6,7,8-tetrahydro-1,8-naphthyridin-3-yl)acrylamide comprising contacting a suspension comprising (E)-N-methyl-N-((3-methylbenzofuran-2-yl)methyl)-3-(7-oxo-5,6,7,8-tetrahydro-1,8-naphthyridin-3-yl)acrylamide with an organic base, for example N,N'-diisopropylethylamine (DI-PEA); heating the suspension; and filtering the suspension to retrieve (E)-N-methyl-N-((3-methylbenzofuran-2-yl)methyl)-3-(7-oxo-5,6,7,8-tetrahydro-1,8-naphthyridin-3-yl)acrylamide.

In some embodiments, the disclosed compounds and/or compostions may be subject to further processing, for example ball milling. In some embodiments, ball milling of a disclosed compound may result in a different, e.g. unique, polymorph of that compound. Ball milling may be performed in various ways as known to those skilled in the art.

For example, ball milling may be conducted by drying the solid compound at, for example, about 50° C. in a vacuum oven for, e.g. about 48 h. The solid can then be milled for example in 12-g batches using a Fritsch Pulverisette 6-ball mill in a 240-mL bowl with 150 agate balls at 200 rpm for 1 min, and then blended in a large beaker.

Other exemplary balling milling procedures that result in particle size reduction include the use of fluid energy jet mills. In this procedure, the material may be manually fed into a hopper placed on top of a feed tray. The material is drawn into a confined, circular chamber by way of pressurized gas and is suspended in a high velocity fluid stream in the milling chamber. The mill operates on the principle of impact and attrition due to the high velocity collisions between particles suspended within the gas stream, causing them to breakdown into smaller particles.

Centrifugal force causes large, heavy particles to separate from smaller and lighter particles. The smaller particles are carried in the fluid stream towards the center of the milling chamber, where they are discharged into a filter bag. The larger particles are thrown outward where they re-circulate and re-collide, causing them to breakdown. Typically, operational parameters are monitored and documented throughout this process.

The disclosed compounds can be characterized by X-ray powder diffractometry (XRPD). An XRPD spectrum may be obtained with a measurement error depending on measurement conditions. In particular, intensities in a XRPD may fluctuate depending on measurement conditions. Therefore, it should be understood that the compounds providing any XRPD spectra substantially the same as the disclosed spectra fall within the scope of the present invention. Those skilled in the art can readily judge the substantial identity of XRPD spectra.

Generally, a measurement error of diffraction angle for a X-ray powder diffractometry is about 5% or less, and such degree of a measurement error should be taken into account as to diffraction angles. For example, the diffraction angles may be reported with a measurement error of ±1°, ±2°, ±3°, or ±5° 2θ.

Method VI
Cis-Isomers

Scheme III shows the conversion of trans isomer to cis isomer by photochemical equilibration.

Scheme III

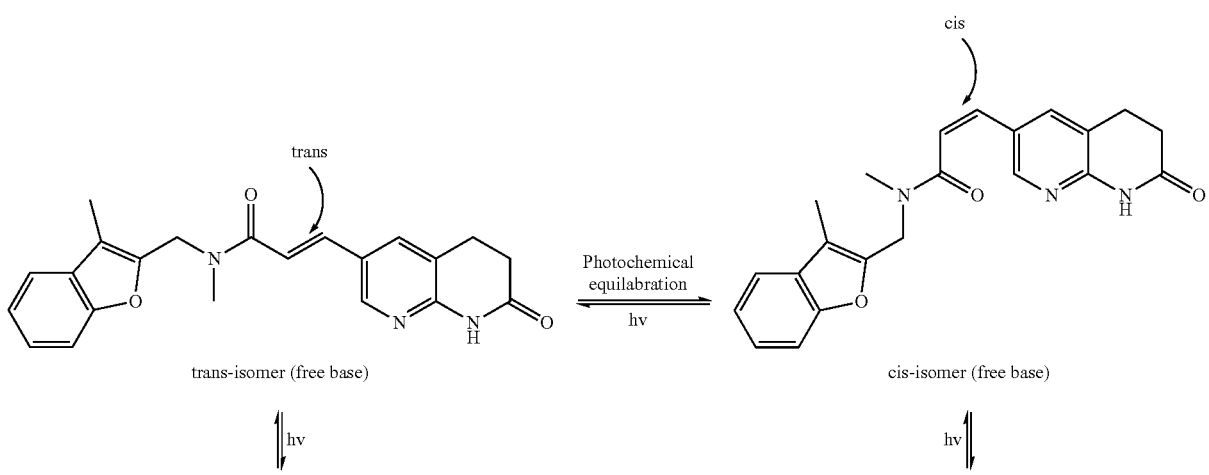

trans-isomer (free base)    cis-isomer (free base)

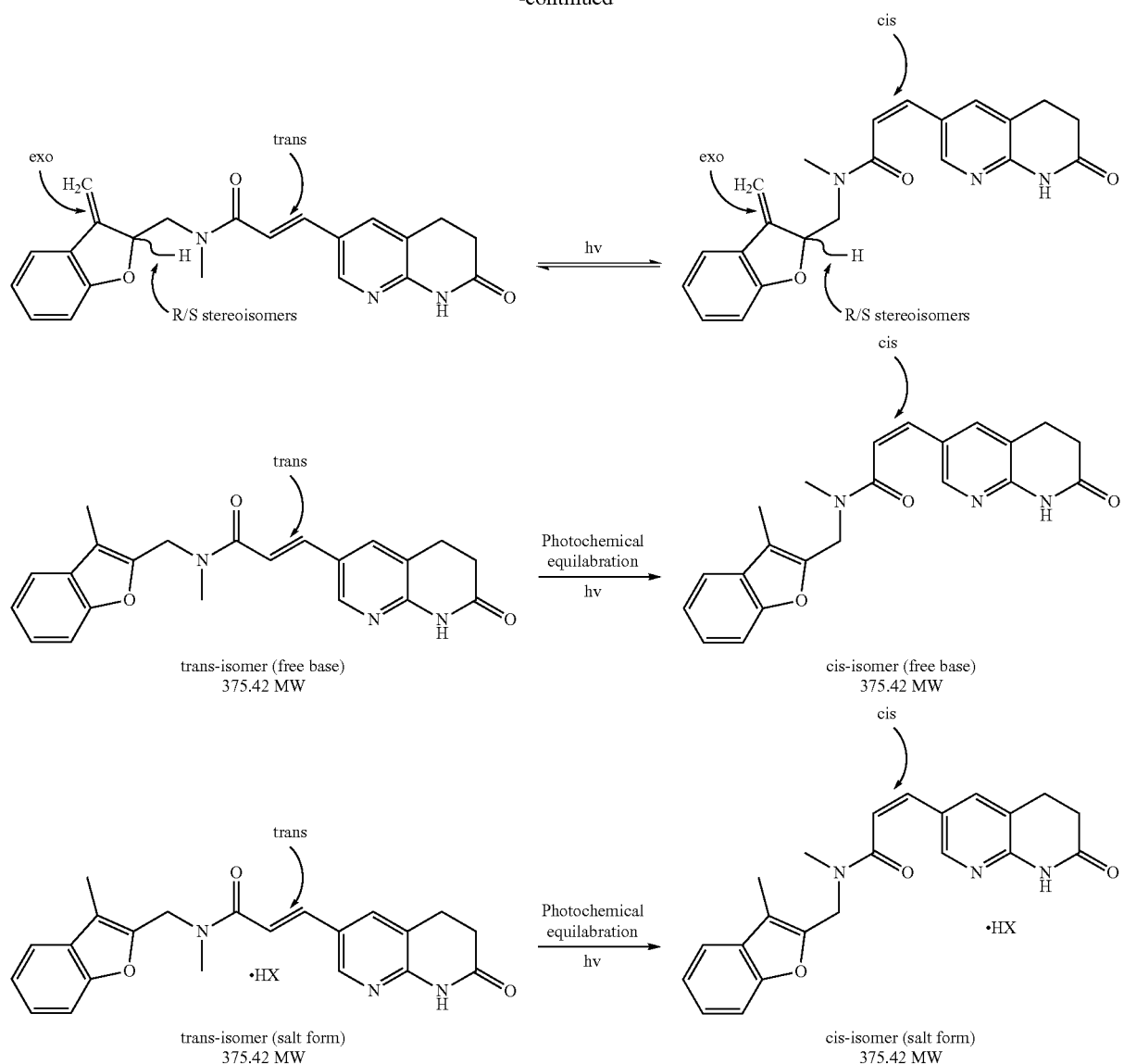

Preparative normal phase high performance liquid chromatography or reverse phase high performance chromatography can isolate the final product.

Toxicology of Compounds

Acute toxicity can be assessed using increasing doses in mice and rodents. Exploratory acute toxicity in mice and/or rats after single dose may be undertaken to begin estimation of the therapeutic window of inhibitors and to identify the potential target organ is of toxicity. As candidate selection nears, these studies may provide guidance for the selection of proper doses in multi-dose studies, as well as establish any species specific differences in toxicities. These studies may be combined with routine PK measurements to assure proper dosages were achieved. Generally 3-4 doses will be chosen that are estimated to span a range having no effect through to higher doses that cause major toxic, but non-lethal, effects. Animals will be observed for effects on body weight, behavior and food consumption, and after euthanasia, hematology, blood chemistry, urinalysis, organ weight, gross pathology and histopathology will be undertaken.

Resistance Frequencies and Mechanisms of Compounds

In vitro resistance frequencies in bacteria of interest can be estimated for compounds of formula I. Experiments can determine whether resistant isolates arise when challenged to grow on solid media at 1×, 2× and 4×MIC concentrations. For example with respect to S. aureus or E. Coli, the experiments may use several recent clinical isolates of methicillin-sensitive and methicillin-resistant S. aureus and a laboratory strain of E. coli with acrA efflux pump defect. In addition, experiments may use several characterized triclosan-resistant S. aureus strains. The MICs of resistant strains isolated in this manner can then be determined. Subsequent experiments can determine whether resistant strains arise after serial passage of the strains in 0.5×MIC concentrations of each lead compound.

Mechanism of resistance may be determined in S. aureus laboratory strain, RN450 and in an E. coli laboratory strain carrying an acrA efflux pump mutation. Both high dose challenge (4×MIC) and sub-MIC serial passage may be used to obtain spontaneously arising resistant isolates. If no isolates are obtained with reasonable frequencies, chemical and physical mutagenesis methods can be used to obtain resistant isolates. The fabI gene from the chromosome of resistant isolates may be PCR amplified, then may be sequenced to determine whether changes in the FabI protein caused resistance. Triplicate PCR amplifications and sequences may be performed to assure that the observed sequence changes are correct, and did not arise from PCR errors during amplification. Strains carrying resistance mutations outside of the gene of interest may be documented and saved, characterized for their effects on susceptibilities of other antibiotics as evidence of possible efflux-mediated resistance mechanisms, characterized for their ability to alter compounds characterized for their effects on the expression of the specific mRNA and FabI protein.

Assays

Many different assay methods can be used to determine the activity of the compounds of the present invention. These assay methods include, for example, the following but also include other methods known to one of ordinary skill in the art.

*S. aureus* FabI Enzyme Inhibition Assay (NADH).

Assays are carried out in half-area, 96-well microtitre plates. Compounds are evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of *S. aureus* FabI. Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Triclosan, a commercial antibacterial agent and inhibitor of FabI, may be included in an assay as a positive control. Compounds of this invention may have $IC_{50}$'s from about 5.0 micromolar to about 0.05 micromolar.

*S. aureus* FabI Enzyme Inhibition Assay (NADPH) (Modified)

Assays are carried out in half-area, 96-well microtitre plates. Compounds are evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of *S. aureus* FabI Inhibitors are typically varied over the range of 0.01-10 uM. The consumption of NADPH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

*H. influenzae* FabI Enzyme Inhibition Assay

Assays are carried out in half-area, 96-well microtiter plates. Compounds are evaluated in 150-uL assay mixtures containing 100 mM MES, 51 mM diethanolamine, 51 mM triethanolamine, pH 6.5 (MES=2-(N-morpholino)ethanesulfonic acid), 4% glycerol, 25 uM crotonoyl-ACP, 50 uM NADH, and an appropriate dilution of *H. influenzae* FabI (approximately 20 nM). Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves. $IC_{50}$'s are estimated from a fit of the initial velocities to a standard, 4-parameter model, and are typically reported as the mean±S.D. of duplicate determinations. The apparent Ki is calculated assuming the inhibition is competitive with crotonoyl-ACP. A proprietary lead compound is currently included in all assays as a positive control.

*E. coli* FabI Enzyme Inhibition Assay

Assays are carried out in half-area, 96-well microtitre plates. Compounds are evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of *E. coli* FabI. Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 100.0 micromolar to about 0.05 micromolar.

Preparation and Purification of Crotonoyl-ACP

Reactions contain 5 mg/mL *E. coli* apo-ACP, 0.8 mM crotonoyl-CoA (Fluka), 10 mM $MgCl_2$, and 30 uM *S. pneumoniae* ACP synthase in 50 mM NaHEPES, pH 7.5. The mixture is gently mixed on a magnetic stirrer at 23° C. for 2 hr, and the reaction is terminated by the addition of 15 mM EDTA and cooling on ice. The reaction mixture is filtered through a 0.2 micron filter (Millipore) and applied to a MonoQ column (Pharmacia) equilibrated with 20 mM Tris-Cl, pH 7.5. The column is washed with buffer until all non-adherent material is removed (as observed by UV detection), and the crotonoyl-ACP is eluted with a linear gradient of 0 to 400 mM NaCl.

*S. aureus* FabI Enzyme Inhibition Assay Using Crotonoyl-ACP

Assays are carried out in half-area, 96-well microtitre plates. Compounds are evaluated in 100 uL assay mixtures containing 100 mM NaADA, pH 6.5 (ADA=N-(2-acetamido)-2-iminodiacetic acid), 4% glycerol, 25 uM crotonoyl-ACP, 50 uM NADPH, and an appropriate dilution of *S. aureus* Fab I (approximately 20 nM) Inhibitors are typically varied over the range of 0.01-30 uM. The consumption of NADPH is monitored for 30 minutes at 30° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent Ki is calculated from Equation 2 assuming the inhibition is competitive with crotonoyl-ACP. More specifically, measured $IC_{50}$ values for 24 compounds of the present invention, as provided in the representative list above, ranged from less than about 0.02 µM to about 25 µM with 11 of these compounds having an $IC_{50}$ of less than 1.

*H. pylori* FabI Enzyme Inhibition Assay Using Crotonoyl-ACP

Assays are carried out in half-area, 96-well microtitre plates. Compounds are evaluated in 100 uL assay mixtures containing 100 mM NaADA, pH 6.5 (ADA=N-(2-acetamido)-2-iminodiacetic acid), 4% glycerol, 10 uM crotonoyl-ACP, 50 uM NADH, 100 mM ammonium acetate, and an appropriate dilution of *H. pylori* Fab I (approximately 15 nM). Inhibitors are typically varied over the range of 0.025-30 uM. The consumption of NADH is monitored for 30 minutes at 25° C. by following the change in absorbance at 340 nm. Initial velocities are estimated from a linear fit of the progress curves. IC50's are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent $K_i$ is calculated from Equation 2 assuming the inhibition is competitive with crotonoyl-ACP.

$$v=\text{Range}/(1+[I]/IC50)s+\text{Background} \quad \text{Equation 1}$$

$$Ki(\text{app})=IC50/(1+[S]/Ks) \quad \text{Equation 2}$$

*S. pneumoniae* FabK Enzyme Inhibition Assay Using Crotonoyl-ACP

Assays are carried out in half-area, 96-well microtitre plates. Compounds are evaluated in 100 uL assay mixtures containing 100 mM MES, 51 mM diethanolamine, 51 mM triethanolamine, pH 6.5 [MES=2-(N-morpholino)ethanesulfonic acid], 4% glycerol buffer, 100 mM NH$_4$Cl, 25 µM crotonoyl-ACP, 50 µM NADH, and 15 nM *S. pneumoniae* FabK. Inhibitors are typically varied over the range of 0.025-30 uM. The consumption of NADH is monitored for 30 minutes at 30° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent $K_i$ is calculated from Equation 2 assuming the inhibition is competitive with crotonoyl-ACP.

Antimicrobial Activity Assay

Whole-cell antimicrobial activity is determined by broth microdilution using the National Committee for Clinical Laboratory Standards (NCCLS) recommended procedure, Document M7-A5, "Methods for Dilution Susceptibility Tests for Bacteria that Grow Aerobically". The compound is tested in serial two-fold dilutions ranging from 0.06 to 64 mcg/mL. A panel of 12 strains are evaluated in the assay. This panel consists of the following laboratory strains: *Enterococcus faecalis* 29212, *Staphylococcus aureus* 29213, *Staphylococcus aureus* 43300, *Moraxella catarrhalis* 49143, *Haemophilus influenzae* 49247, *Streptococcus pneumoniae* 49619, *Staphylococcus epidermidis* 1024939, *Staphylococcus epidermidis* 1024961, *Escherichia coli* AG100 (AcrAB$^+$), *Escherichia coli* AG100A (AcrAB$^-$), *Pseudomonas aeruginosa* K767 (MexAB$^+$, OprM$^+$), *Pseudomonas aeruginosa* K1119 (MexAB$^-$, OprM$^-$). The minimum inhibitory concentration (MIC) is determined as the lowest concentration of compound that inhibited visible growth. A spectrophotometer is used to assist in determining the MIC endpoint.

MIC assays may be performed using the microdilution method in a 96 well format. The assays may be performed in 96 well plates with a final volume of 100 µl cation-adjusted Mueller Hinton broth containing 2 fold serial dilutions of compounds ranging from 32 to 0.06 µg/ml. Bacterial growth may be measured at 600 nm using a Molecular Devices SpectraMax 340PC spectrophotometer. MICs can then be determined by an absorbance threshold algorithm and confirmed in some cases by inspecting the plates over a light box.

Minimum Bactericidal Concentration (MBC) may be determined by plating aliquots of MIC dilution series that did not show bacterial growth onto Petri plates containing appropriate semi-solid growth media. The lowest compound concentration that resulted in >99% killing of bacterial cells (relative to initial bacterial inocula in MIC test) is defined as the MBC.

Several strain panels may be used at various points in the compound progression scheme. The primary panel may include single prototype strains of both community- and hospital-acquired pathogens for determining initial activities and spectra of activity. Secondary panel compositions will depend on the results of the primary panels, and will include 10-20 strains of relevant species that will include community acquired and antibiotic-resistant hospital acquired strains of *Staphylococcus aureus* and coagulase negative Staphylococci together with other strains that are sensitive to the new compounds, and negative control strains. The secondary panels will be used during optimization of lead chemical series. Tertiary panels will include 100-200 clinical strains of *S. aureus* and coagulase negative Staphylococci together with other relevant strains as for the secondary panels. The tertiary panels will be utilized during the compound candidate selection stage and preclinical studies to generate bacterial population efficacy parameters such as $MIC_{50}$ and $MIC_{90}$.

*Franciscella tularensis* In Vitro Efficacy Studies

Routine MIC testing of *F. tularensis* may be undertaken on compounds that have demonstrated enzymatic activity inhibition against the *F. tularensis* FabI protein. The MIC testing of *F. tularensis* may be outsourced to a facility with BL3 capabilities, and with experience in handling *F. tularensis* cultures in the laboratory. The studies may be undertaken with the recommended methods for antimicrobial susceptibility testing of *F. tularensis.*

*Helicobacter pylori* In Vitro Efficacy Studies

Routine MIC testing of *H. pylori* may be undertaken on compounds that have demonstrated enzymatic activity inhibition against the *H. pylori* FabI protein. The studies may be undertaken with the recommended methods for antimicrobial susceptibility testing of *H. pylori.*

Cytotoxicity Assays

Cytotoxicity of the new compounds may be evaluated by the Alamar Blue assay according the manufacturers instructions. Human cell lines (e.g. Jurkat) grown in 96 well plates may be exposed to serial dilutions of the tested compounds. After adding Alamar Blue, cell viability may be determined by measuring the absorbance of the reduced and oxidized forms of Alamar Blue at 570 nm and 600 nm. Cytotoxicity may be reported as $LD_{50}$, the concentration that causes a 50% reduction in cell viability.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the FabI inhibitor) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Combinations

Compositions are also contemplated herein that include one or more of the disclosed antibacterial compounds with a second component. Second components in such antibacterial compositions of the present invention are usually an antibiotic agent other than a FabI inhibitor. Additional components may also be present, including other FabI inhibitors or antibiotic agents.

Non-limiting examples of antibiotic agents that may be used in the antibacterial compositions of the present invention include cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and others. Each family comprises many members.

Cephalosporins are further categorized by generation. Non-limiting examples of cephalosporins by generation include the following. Examples of cephalosporins I generation include Cefadroxil, Cefazolin, Cephalexin, Cephalothin, Cephapirin, and Cephradine. Examples of cephalosporins II generation include Cefaclor, Cefamandol, Cefonicid, Cefotetan, Cefoxitin, Cefprozil, Ceftmetazole, Cefuroxime, Cefuroxime axetil, and Loracarbef. Examples of cephalosporins III generation include Cefdinir, Ceftibuten, Cefditoren, Cefetamet, Cefpodoxime, Cefprozil, Cefuroxime (axetil), Cefuroxime (sodium), Cefoperazone, Cefixime, Cefotaxime, Cefpodoxime proxetil, Ceftazidime, Ceftizoxime, and Ceftriaxone. Examples of cephalosporins IV generation include Cefepime.

Non-limiting examples of quinolones and fluoroquinolones include Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, and Pefloxacin.

Non-limiting examples of penicillins include Amoxicillin, Ampicillin, Bacampicillin, Carbenicillin Indanyl, Mezlocillin, Piperacillin, and Ticarcillin.

Non-limiting examples of penicillins and beta lactamase inhibitors include Amoxicillin-Clavulanic Acid, Ampicillin-Sulbactam, Benzylpenicillin, Cloxacillin, Dicloxacillin, Methicillin, Oxacillin, Penicillin G (Benzathine, Potassium, Procaine), Penicillin V, Piperacillin+Tazobactam, Ticarcillin+Clavulanic Acid, and Nafcillin.

Non-limiting examples of carbepenems include Imipenem-Cilastatin and Meropenem.

A non-limiting example of a monobactam includes Aztreonam. Non-limiting examples of macrolides and lincosamines include Azithromycin, Clarithromycin, Clindamycin, Dirithromycin, Erythromycin, Lincomycin, and Troleandomycin. Non-limiting examples of glycopeptides include Teicoplanin and Vancomycin. Non-limiting examples of rifampins include Rifabutin, Rifampin, and Rifapentine. A non-limiting example of oxazolidonones includes Linezolid. Non-limiting examples of tetracyclines include Demeclocycline, Doxycycline, Methacycline, Minocycline, Oxytetracycline, Tetracycline, and Chlortetracycline.

Non-limiting examples of aminoglycosides include Amikacin, Gentamicin, Kanamycin, Neomycin, Netilmicin, Streptomycin, Tobramycin, and Paromomycin. A non-limiting example of streptogramins includes Quinopristin+Dalfopristin.

Non-limiting examples of sulfonamides include Mafenide, Silver Sulfadiazine, Sulfacetamide, Sulfadiazine, Sulfamethoxazole, Sulfasalazine, Sulfisoxazole, Trimethoprim-Sulfamethoxazole, and Sulfamethizole.

Non-limiting examples of other antibiotic agents include Bacitracin, Chloramphenicol, Colistemetate, Fosfomycin, Isoniazid, Methenamine, Metronidazol, Mupirocin, Nitrofurantoin, Nitrofurazone, Novobiocin, Polymyxin B, Spectinomycin, Trimethoprim, Colistin, Cycloserine, Capreomycin, Pyrazinamide, Para-aminosalicyclic acid, and Erythromycin ethylsuccinate+sulfisoxazole.

Formulations

The antibacterial compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In certain embodiments, the subject compounds may be formulated as a tablet, pill capsule or other appropriate ingestible formulation (collectively hereinafter "tablet"), to provide a therapeutic dose in 10 tablets or fewer. In another example, a therapeutic dose is provided in 50, 40, 30, 20, 15, 10, 5 or 3 tablets.

In a certain embodiment, the antibacterial agent is formulated for oral administration as a tablet or an aqueous solution or suspension. In another embodiment of the tablet form of the antibacterial agent, the tablets are formulated such that the amount of antibacterial agent (or antibacterial agents) provided in 20 tablets, if taken together, would provide a dose of at least the median effective dose ($ED_{50}$), e.g., the dose at which at least 50% of individuals exhibited the quantal effect of inhibition of bacterial cell growth or protection (e.g., a statistically significant reduction in infection). In a further embodiment, the tablets are formulated such that the total amount of antibacterial agent (or antibacterial agents) provided in 10, 5, 2 or 1 tablets would provide at least an $ED_{50}$ dose to a patient (human or non-human mammal). In other embodiments, the amount of antibacterial agent (or antibacterial agents) provided in 20, 10, 5 or 2 tablets taken in a 24 hour time period would provide a dosage regimen providing, on average, a mean plasma level of the antibacterial agent(s) of at least the $ED_{50}$ concentration (the concentration for 50% of maximal effect of, e.g., inhibiting bacterial cell growth). In other embodiments less than 100 times, 10 times, or 5 times the ED50 is provided. In other embodiments, a single dose of tablets (1-20 tablets) provides about 0.25 mg to 1250 mg of an antibacterial agent(s).

Likewise, the antibacterial agents can be formulated for parenteral administration, as for example, for subcutaneous, intramuscular or intravenous injection, e.g., the antibacterial agent can be provided in a sterile solution or suspension (collectively hereinafter "injectable solution"). The injectable solution is formulated such that the amount of antibacterial agent (or antibacterial agents) provided in a 200 cc bolus injection would provide a dose of at least the median effective dose, or less than 100 times the $ED_{50}$, or less than 10 or 5 times the $ED_{50}$. The injectable solution may be formulated such that the total amount of antibacterial agent (or antibacterial agents) provided in 100, 50, 25, 10, 5, 2.5, or 1 cc injections would provide an $ED_{50}$ dose to a patient, or less than 100 times the $ED_{50}$, or less than 10 or 5 times the $ED_{50}$. In other embodiments, the amount of antibacterial agent (or antibacterial agents) provided in a total volume of 100 cc, 50, 25, 5 or 2 cc to be injected at least twice in a 24 hour time period would provide a dosage regimen providing, on average, a mean plasma level of the antibacterial agent(s) of at least the $ED_{50}$ concentration, or less than 100 times the $ED_{50}$, or less than 10 or 5 times the $ED_{50}$. In other embodiments, a single dose injection provides about 0.25 mg to 1250 mg of antibacterial agent.

Efficacy of Treatment

The efficacy of treatment with the subject compositions may be determined in a number of fashions known to those of skill in the art.

In one exemplary method, the median survival rate of the bacteria or bacteria median survival time or life span for treatment with a subject composition may be compared to other forms of treatment with the particular FabI inhibitor, or with other antibiotic agents. The decrease in median bacteria survival rate or time or life span for treatment with a subject composition as compared to treatment with another method may be 10, 25, 50, 75, 100, 150, 200, 300, 400% even more. The period of time for observing any such decrease may be about 3, 5, 10, 15, 390, 60 or 90 or more days. The comparison may be made against treatment with the particular FabI inhibitor contained in the subject composition, or with other antibiotic agents, or administration of the same or different agents by a different method, or administration as part of a different drug delivery device than a subject composition. The comparison may be made against the same or a different effective dosage of the various agents. The different regiments compared may use measurements of bacterial levels to assess efficacy.

Alternatively, a comparison of the different treatment regimens described above may be based on the effectiveness of the treatment, using standard indicies for bacterial infections known to those of skill in the art. One method of treatment may be 10%, 20%, 30%, 50%, 75%, 100%, 150%, 200%, 300% more effective, than another method.

Alternatively, the different treatment regimens may be analyzed by comparing the therapeutic index for each of them, with treatment with a subject composition as compared to another regimen having a therapeutic index two, three, five or seven times that of, or even one, two, three or more orders of magnitude greater than, treatment with another method using the same or different FabI inhibitor.

As a non-limiting example, to determine if compounds are bactericidal or bacteriostatic at relevant concentrations, and to examine the kinetics of bacterial killing the following experiment may be performed with S. aureus, S. epidermidis and appropriate control strains and antibiotics. To fresh logarithmic cultures at $10^7$ viable cells/ml, compound may be added to reach concentrations of ×1, ×2 or ×4 the MIC. Control cultures will receive no compound. At 1 hour intervals, aliquots will be diluted and plated for determining viable counts. Plots of viable cells vs. time for up to 24 hours will reveal bactericidal/bacteriostatic properties of the compounds, and also show the kill kinetics. These experiments are important to determine whether these inhibitors have time-dependent or concentration-dependent effects, and will be used to help set appropriate dosages in vivo in combination with pharmacokinetic and pharmacodynamic measurements.

In the practice of the instant methods, the antibacterial compositions of the present invention inhibit bacterial FabI with a $K_i$ of 5 μM or less, 1 μM or less, 100 nM or less, 10 nM or less or even 1 nM or less. In treatment of humans or other animals, the subject method may employ FabI inhibitors which are selective for the bacterial enzyme relative to the host animals' enoyl CoA hydratase, e.g., the $K_i$ for inhibition of the bacterial enzyme is at least one order, two orders, three orders, or even four or more orders of magnitude less than the $K_i$ for inhibition of enoyl CoA hydratase from the human (or other animal). That is, the practice of the subject method in vivo in animals utilizes FabI inhibitors with therapeutic indexes of at least 10, 100 or 1000.

Similarly, in the practice of the instant method, the antibacterial compounds of the present invention inhibit FabI with an $IC_{50}$ of 30 μM or less, 10 μM or less, 100 nM or less, or even 10 nM or less. In treatment of humans or other animals, the subject method may employ FabI inhibitors which are selective for the bacterial enzyme relative to the host animals' enoyl CoA hydratase, e.g., the $IC_{50}$ for inhibition of the bacterial enzyme is at least one order, two orders, three orders, or even four orders of magnitude less than the $IC_{50}$ for inhibition of enoyl CoA hydratase from the human (or other animal). That is, in preferred embodiments, the practice of the subject method in vivo in animals utilizes FabI inhibitors with therapeutic indexes of at least 10, 100 or 1000.

Alternatively, bacterial inhibition by an antibacterial compound of the present invention may also be characterized in terms of the minimum inhibitory concentration (MIC), which is the highest concentration of compound required to achieve complete inhibition of bacterial cell growth. Such values are well known to those in the art as representative of the effectiveness of a particular antibacterial agent against a particular organism or group of organisms. In the practice of the instant methods, the antibacterial compositions of the present invention inhibit bacterial growth with MIC values of about 32 μg/mL, less than about 16 μg/mL, less than about 8 μg/mL, less than about 4 μg/mL, less than about 2 μg/mL, less than about 1 μg/mL, less than about 0.5 μg/mL, less than about 0.25 μg/mL, or even less than about 0.125 μg/mL. The value of MIC90, defined as the concentration of a compound required to inhibit the growth of 90% of bacterial strains within a given bacterial strain population, can also be used. In certain embodiments, the compounds of the present invention are selected for use based, inter alia, on having MIC90 values of less than about 32 μg/mL, less than about 16 μg/mL, less than about 8 μg/mL, less than about 4 μg/mL, less than about 2 μg/mL, less than about 1 μg/mL, less than about 0.5 μg/mL, less than about 0.25 μg/mL, or even less than about 0.125 μg/mL.

In other embodiments, the subject compounds are selected for use in animals, or animal cell/tissue culture based at least in part on having $LD_{50}$'s at least one order, or two orders, or three orders, or even four orders or more of magnitude greater than the $ED_{50}$. That is, in certain embodiments where the subject compounds are to be administered to an animal, a suitable therapeutic index is preferably greater than 10, 100, 1000 or even 10,000.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

The examples which follow are intended in no way to limit the scope of this invention but are provided to illustrate how to prepare and use compounds of the present invention. Many other embodiments of this invention will be apparent to one skilled in the art.

EXAMPLES

General

Figure 1:
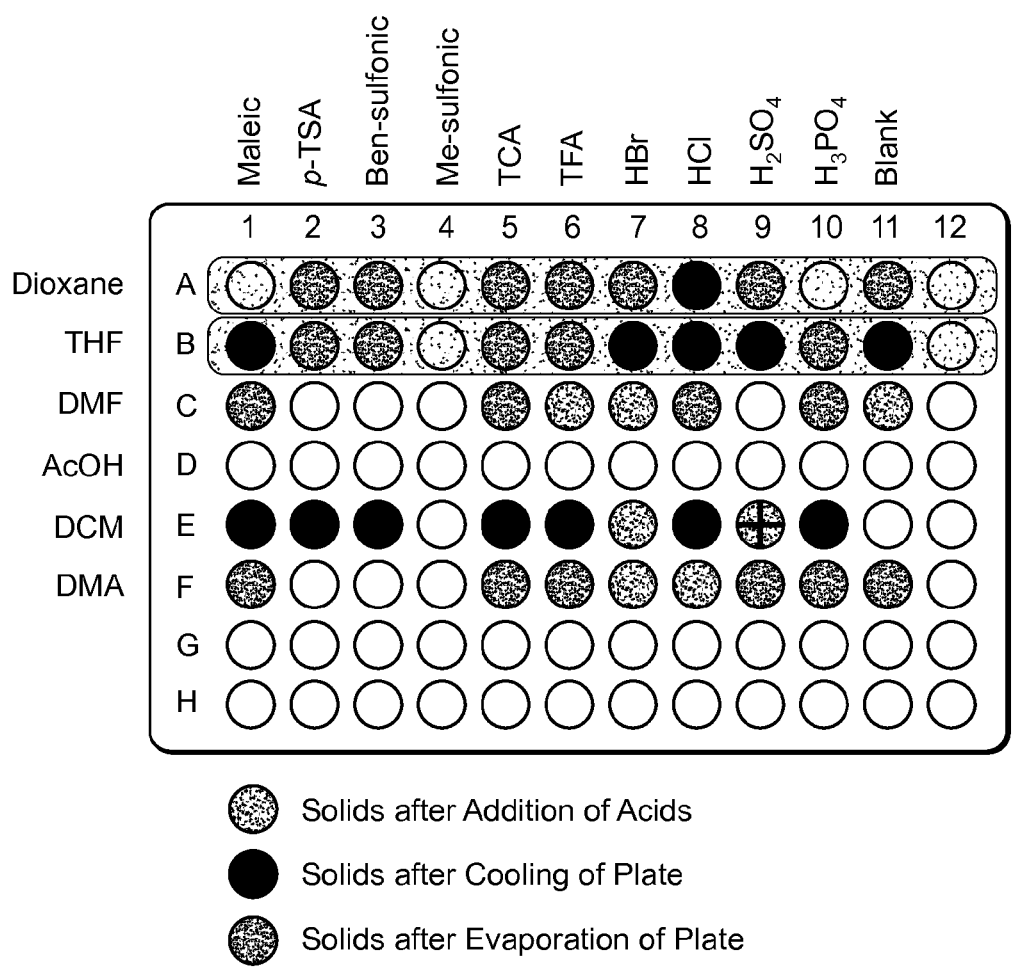
FIG. 1 depicts a 96-well plate for salt formation after acid addition, and cooling and evaporation of the plate.
Figure 2:
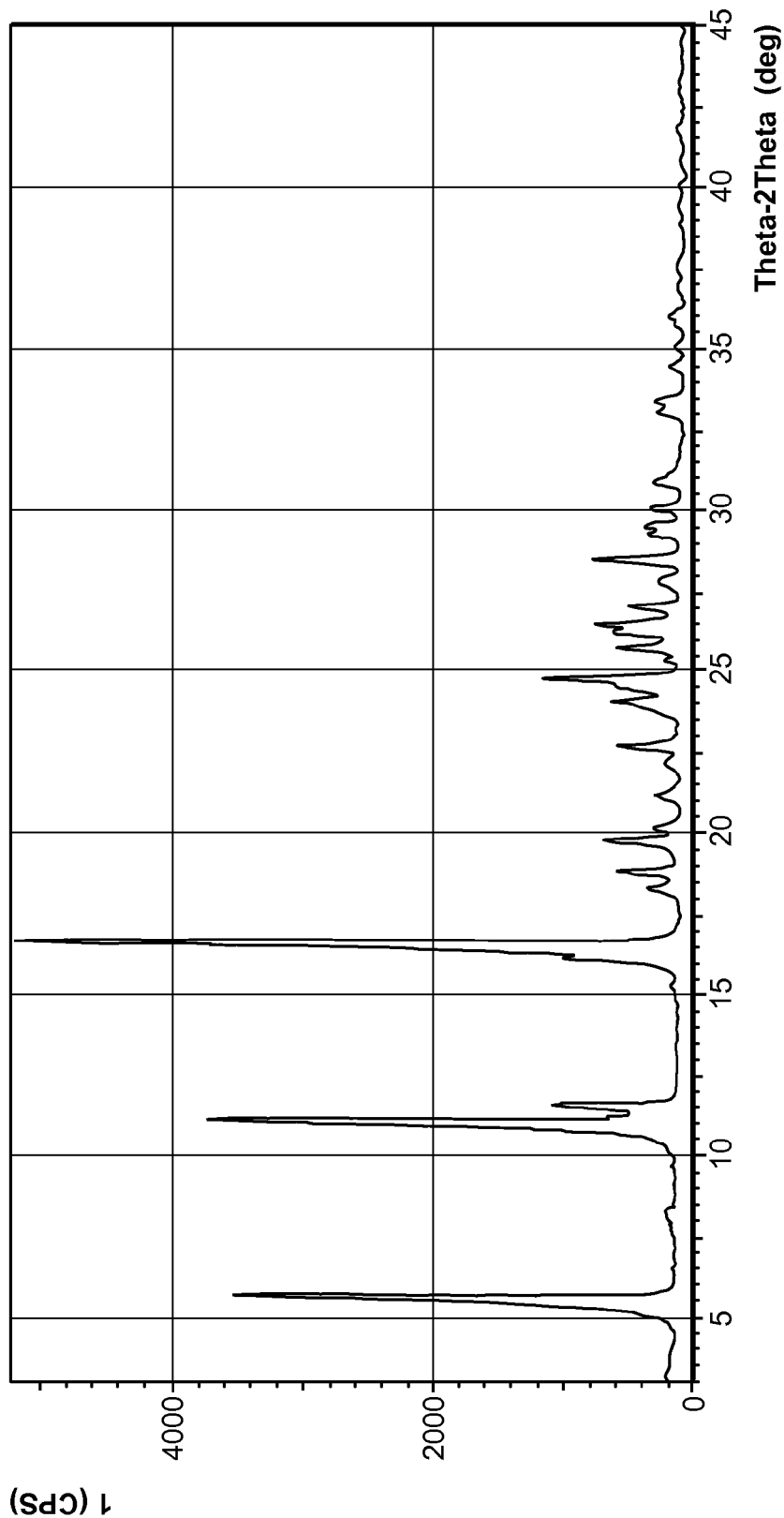
FIG. 2 depicts an XRPD spectra of (E)-N-methyl-N-((3-methylbenzofuran-2-yl)methyl)-3-(7-oxo-5,6,7,8-tetrahydro-1,8-naphthyridin-3-yl)acrylamide.

FIG. 1 shows a 96-well plate after the addition of acid, after the cooling down of the plate, and after evaporation of solvent using Scheme 1. Red wells were solids that precipitated out of solution upon the addition of the acid to the Compound A solution. Blue wells were solids that precipitated out of solution when the plate had reached room temperature. Purple wells had solids after removal of the solvent. Wells with no color are wells that did not produce solids. The black "X" in the DCM/sulfuric is a well in which the solid disappeared, possible due to this solid being deliquescent. The $11^{th}$ "blank" well was charged with (E)-N-methyl-N-((3-methylbenzofuran-2-yl)methyl)-3-(7-oxo-5,6,7,8-tetrahydro-1,8-naphthyridin-3-yl)acrylamide (compound A) and used as a control to monitor the crystallization of free base in the different solvents.

Determination of crystallinity was performed on solid-containing wells by dispersing the solids in mineral oil and using a polarized light microscope at 100× and 400×. Samples which contained particles with distinct birefringence and extinction positions were identified as crystalline. Those which had some particles which exhibited birefringence and extinction positions but also had a significant amount of particles which were not observed to reflect light were described as partially crystalline. Amorphous solids were those which did not have significant amount of particles that reflected polarized light while deliquescent material either became liquid-like or softened during analysis. Counter-ions which were found to exhibit the crystalline to partially crystalline material included maleic, TCA, TFA, HCl, phosphoric acid, benzenesulfonic, methansulfonic, HBr, and sulfuric. All solvents produced crystalline material with THF, AcOH, DCM, and DMA producing at least 3 crystalline solids.

Example 1

Figure 3A:
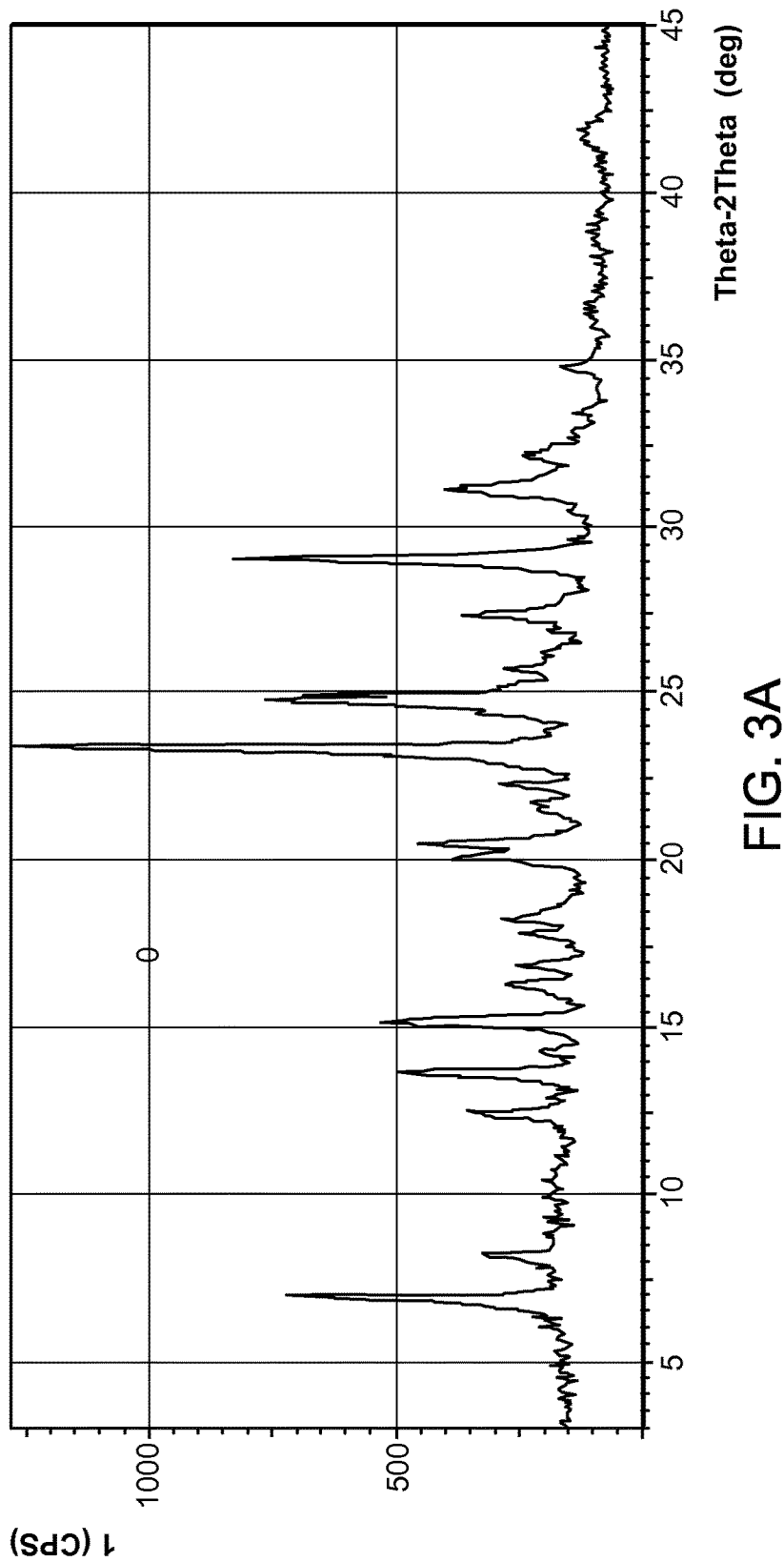
FIG. 3A depicts an XRPD spectra of a hydrochloric acid salt of (E)-N-methyl-N-((3-methylbenzofuran-2-yl)methyl)-3-(7-oxo-5,6,7,8-tetrahydro-1,8-naphthyridin-3-yl)acrylamide
Figure 3B:
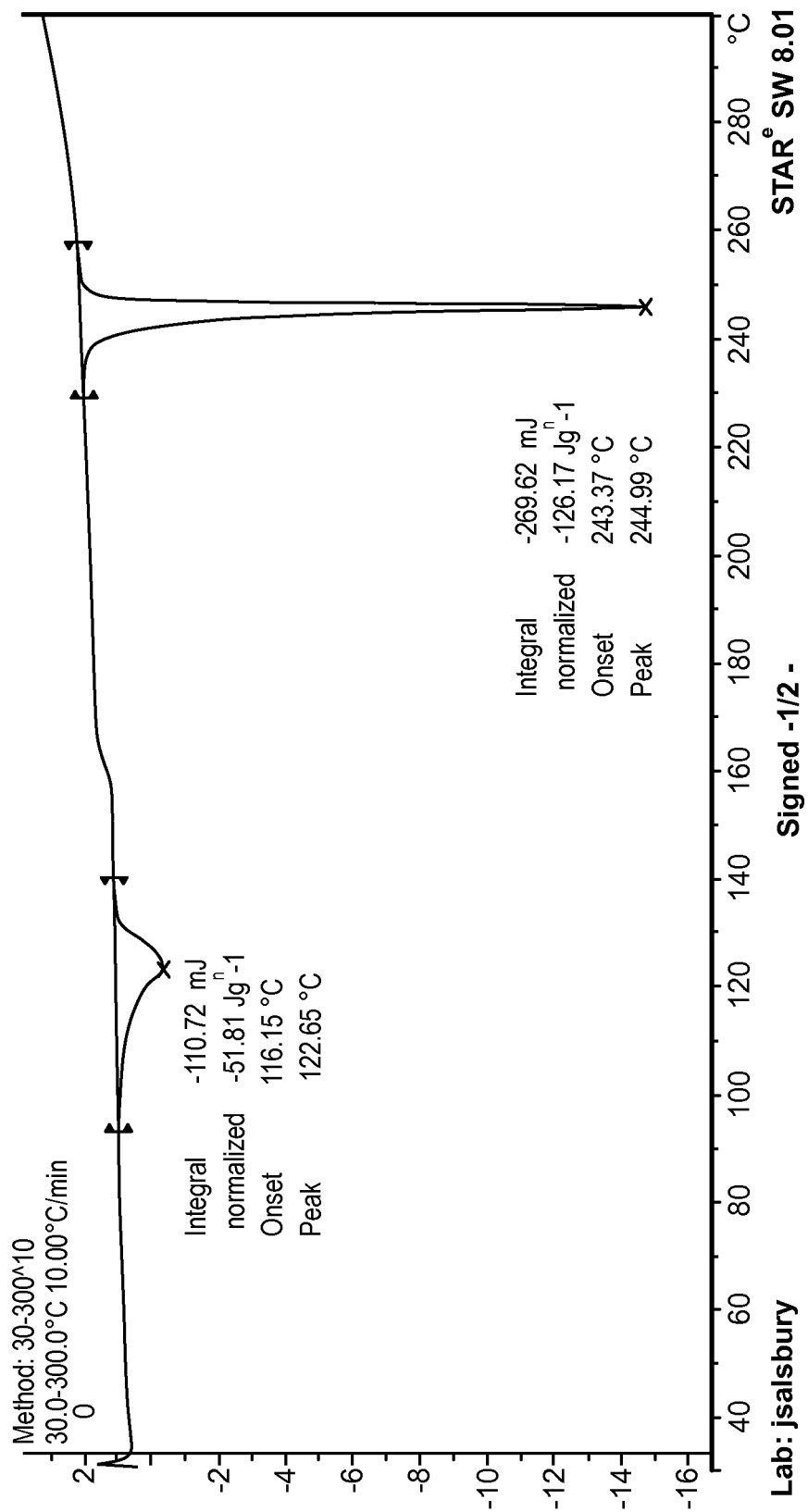
FIG. 3B depicts the DSC of this salt.

(E)-N-methyl-N-((3-methylbenzofuran-2-yl)methyl)-3-(7-oxo-5,6,7,8-tetrahydro-1,8-naphthyridin-3-yl) acrylamide hydrochloride Using method IIA, the vial containing the starting compound A, HCl and DCM solvent, upon cooling, yielded the title compound as a white solid. XRPD analysis indicated a crystalline solid distinct from the free base (compound A). The XRPD spectra is as shown in FIG. 3A. High intensity peaks include those occurring at 6.75, 8.25, 12.5, 16, 17, 17.75, 18, 20.25, 20.5, 23, 24.5, 27.5, 29, 31, and 32 2θ. The DSC of the solid HCL salt showed two thermal events, as depicted in FIG. 3B.

Example 2

(E)-N-methyl-N-((3-methylbenzofuran-2-yl)methyl)-3-(7-oxo-5,6,7,8-tetrahydro-1,8-naphthyridin-3-yl) acrylamide trifluoroacetate Using method IIA, the vial containing compound A, trifluoroacetic acid and acetic acid solvent, upon cooling, yielded the title compound as a white solid. XRPD analysis indicated a crystalline solid distinct from the free base.

Example 3

Figure 4:
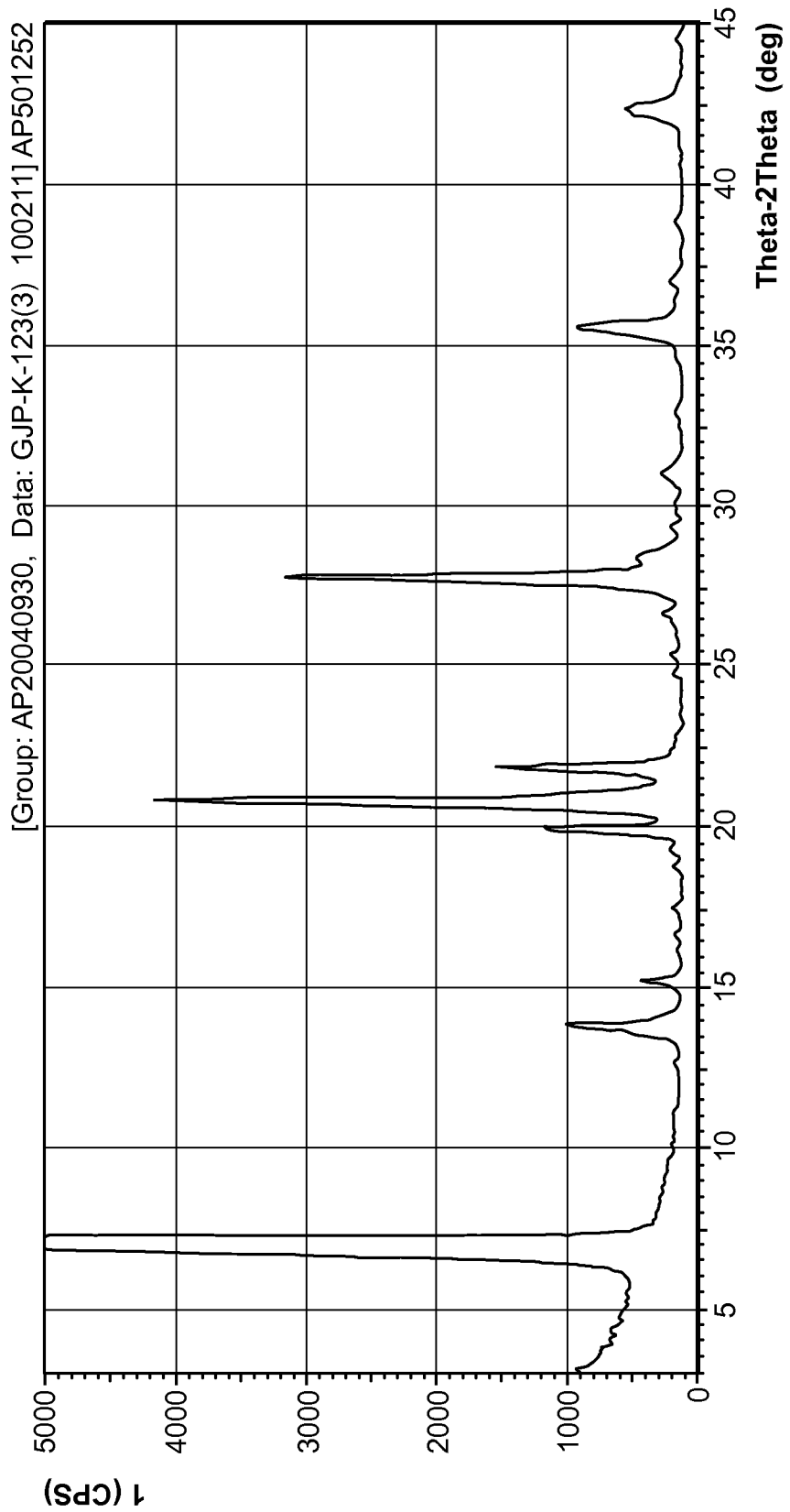
FIG. 4 depicts an XRPD spectra of a mesylate salt of (E)-N-methyl-N-((3-methylbenzofuran-2-yl)methyl)-3-(7-oxo-5,6,7,8-tetrahydro-1,8-naphthyridin-3-yl)acrylamide.

(E)-N-methyl-N-((3-methylbenzofuran-2-yl)methyl)-3-(7-oxo-5,6,7,8-tetrahydro-1,8-naphthyridin-3-yl) acrylamide methane sulfonate Compound A, methane sulfonic acid and THF were processed as described in method IIB (Table 1) above. A solid crystallized during the cooling phase which was isolated as the title compound. The product showed a unique diffraction (XRPD) as compared to the free base as shown in FIG. 4. High intensity peaks include those occurring at 7, 14, 15.5, 20, 21, 23, 28, 35.5 and 42.5 2θ. Two thermal events were seen (DSC)

In a similar manner from DCM upon concentration (about half volume reduction), crystallization occurred to yield the title compound: unique XRPD; mp 187° C.; (DSC); $^1$H-NMR supports an assignment with the ratio between compound and counter-ion being 1:1; the material also showed no retained solvent by weight loss in the TGA.

Example 4

Figure 5:
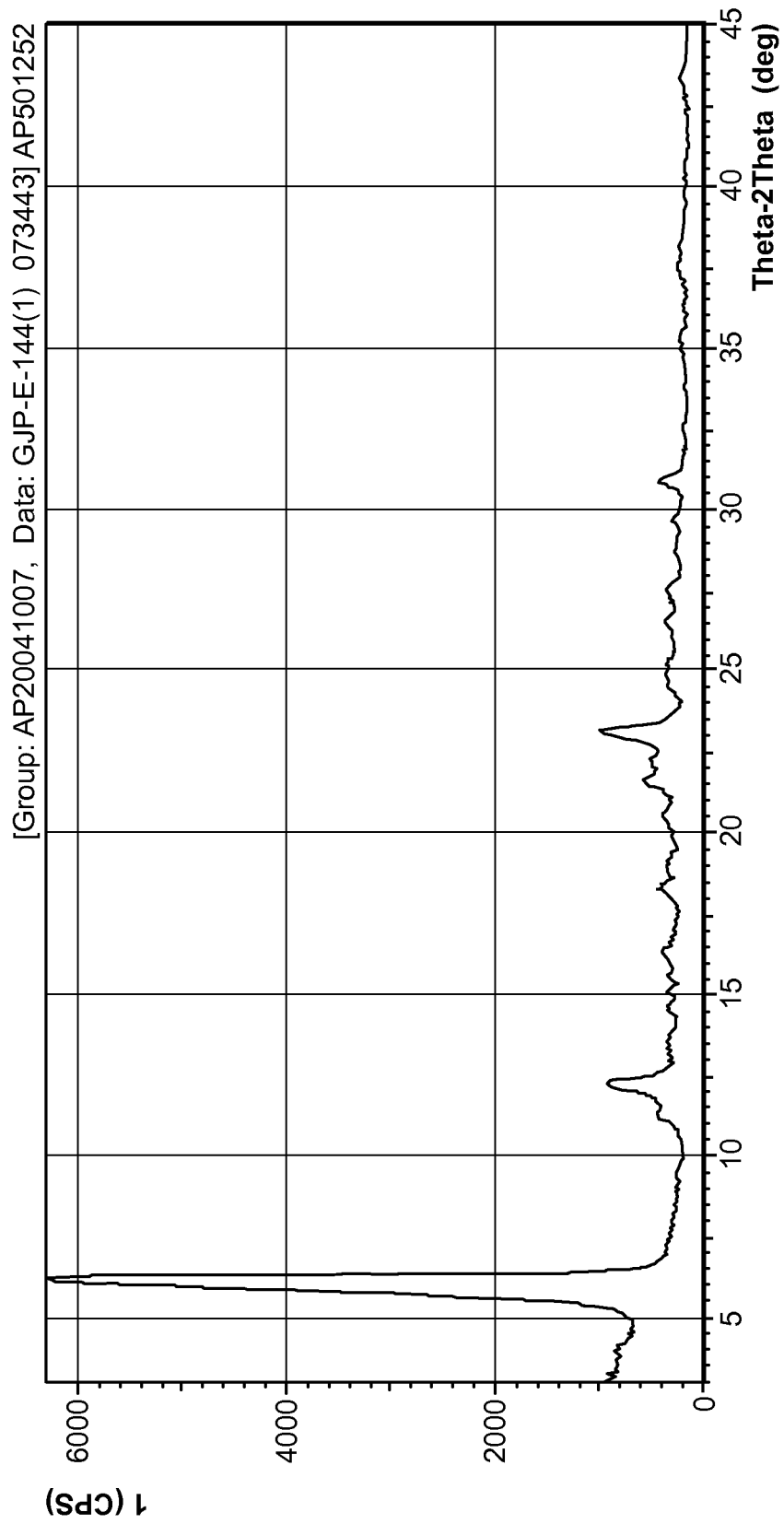
FIG. 5 depicts an XRPD spectra of benzenesulfonic acid salt from THF of (E)-N-methyl-N-((3-methylbenzofuran-2-yl)methyl)-3-(7-oxo-5,6,7,8-tetrahydro-1,8-naphthyridin-3-yl)acrylamide.

(E)-N-methyl-N-((3-methylbenzofuran-2-yl)methyl)-3-(7-oxo-5,6,7,8-tetrahydro-1,8-naphthyridin-3-yl) acrylamide benzene sulfonate Compound A, benzene sulfonic acid and THF were processed as described in method IIB (Table 1). A solid crystallized during the cooling phase which was isolated as the title compound. The product showed a unique diffraction (XRPD) as compared to the free base as shown in FIG. 5; (high intensity peaks include those occurring at 6, 12, 23.5 and 31 2θ); mp 172° C. (DSC); the $^1$H-NMR supported a ratio between the free base and counter-ion of 1:1.

Figure 6:
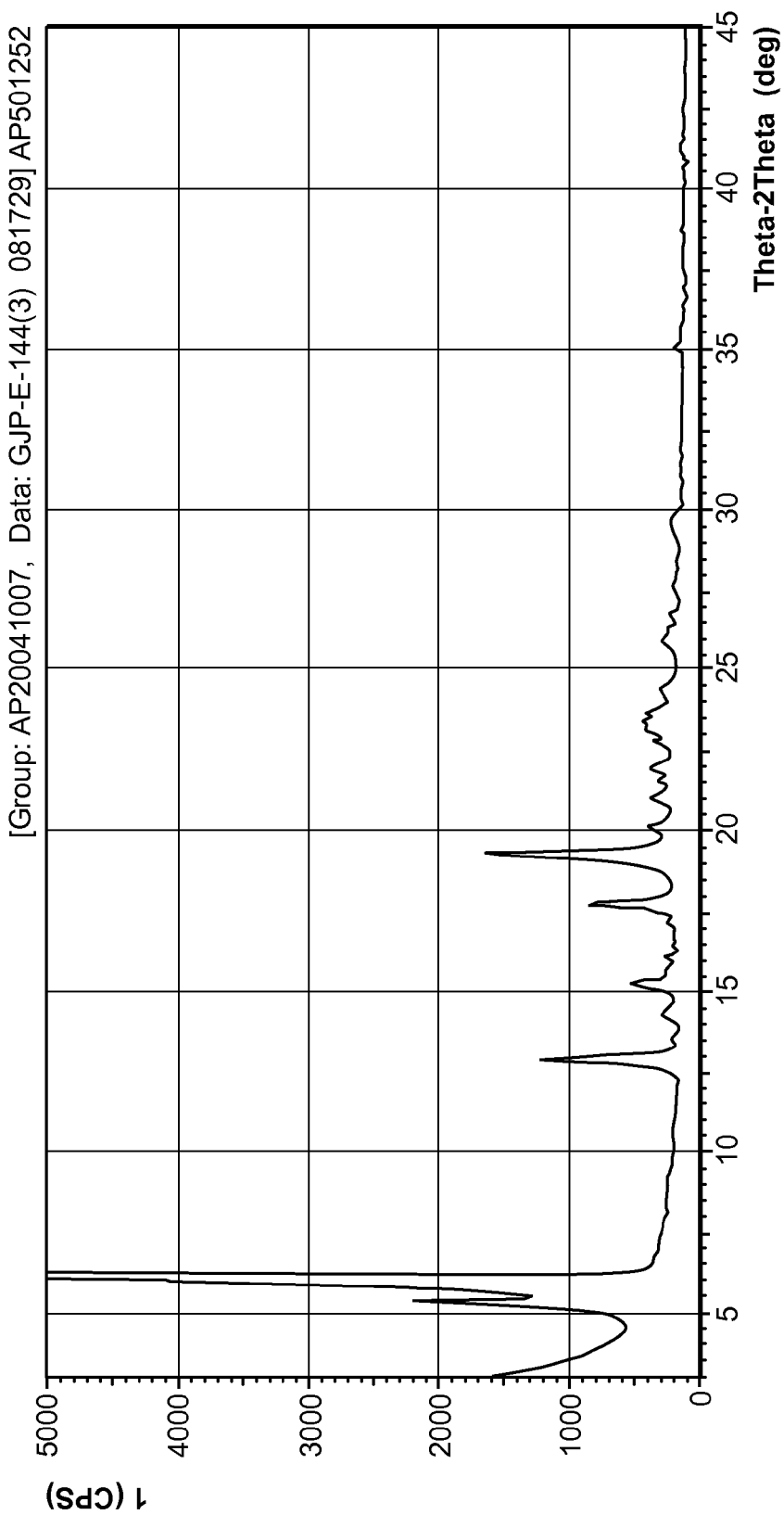
FIG. 6 depicts an XRPD spectra of benzenesulfonic salt from DCM of (E)-N-methyl-N-((3-methylbenzofuran-2-yl)methyl)-3-(7-oxo-5,6,7,8-tetrahydro-1,8-naphthyridin-3-yl) acrylamide.

In a similar manner from DCM upon concentration (about half volume reduction), crystallization occurred to yield the title compound: unique XRPD as shown in FIG. 6 (high intensity peaks include those occurring at 5.5, 6, 13, 15.5, 18 and 19 2θ); mp 168° C.; (DSC), $^1$H-NMR supports an assignment with the ratio between free base and counter-ion being 1:1.

Example 5

Figure 7A:
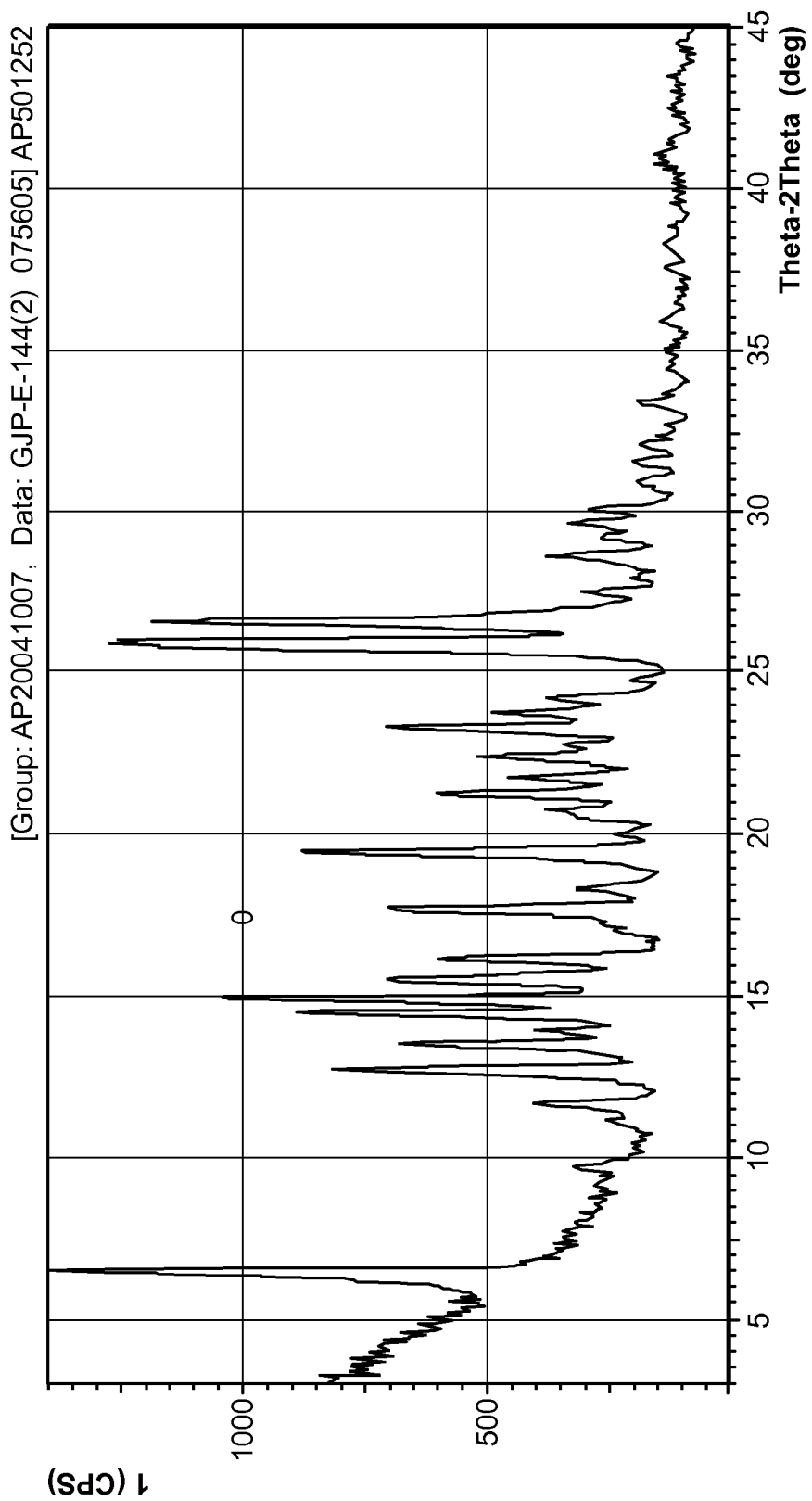
FIG. 7A depicts an XRPD spectra of p-toluenesulfonic salt of (E)-N-methyl-N-((3-methylbenzofuran-2-yl)methyl)-3-(7-oxo-5,6,7,8-tetrahydro-1,8-naphthyridin-3-yl)acrylamide.
Figure 7B:
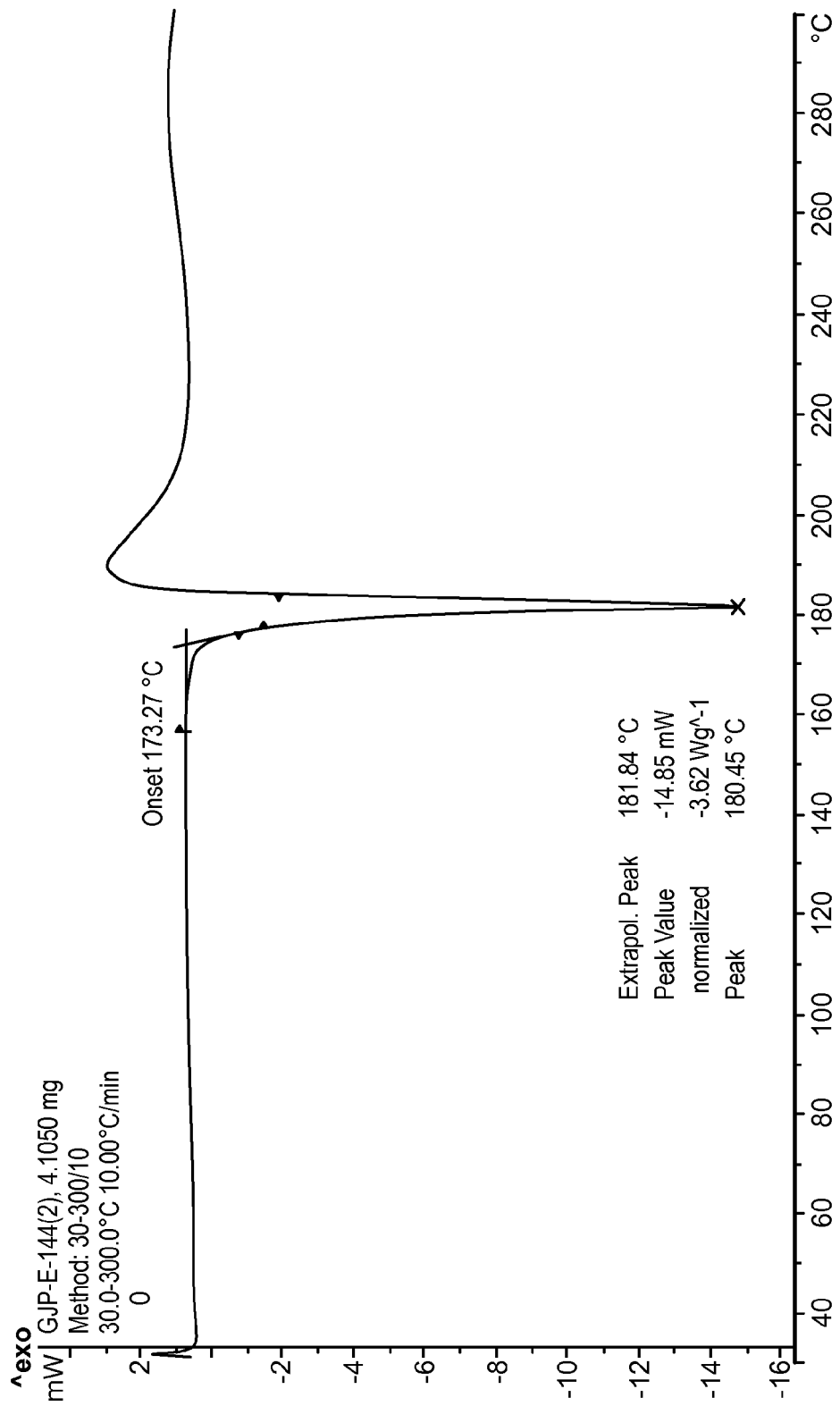
FIG. 7B depicts the DSC of this salt from THF.
Figure 7C:
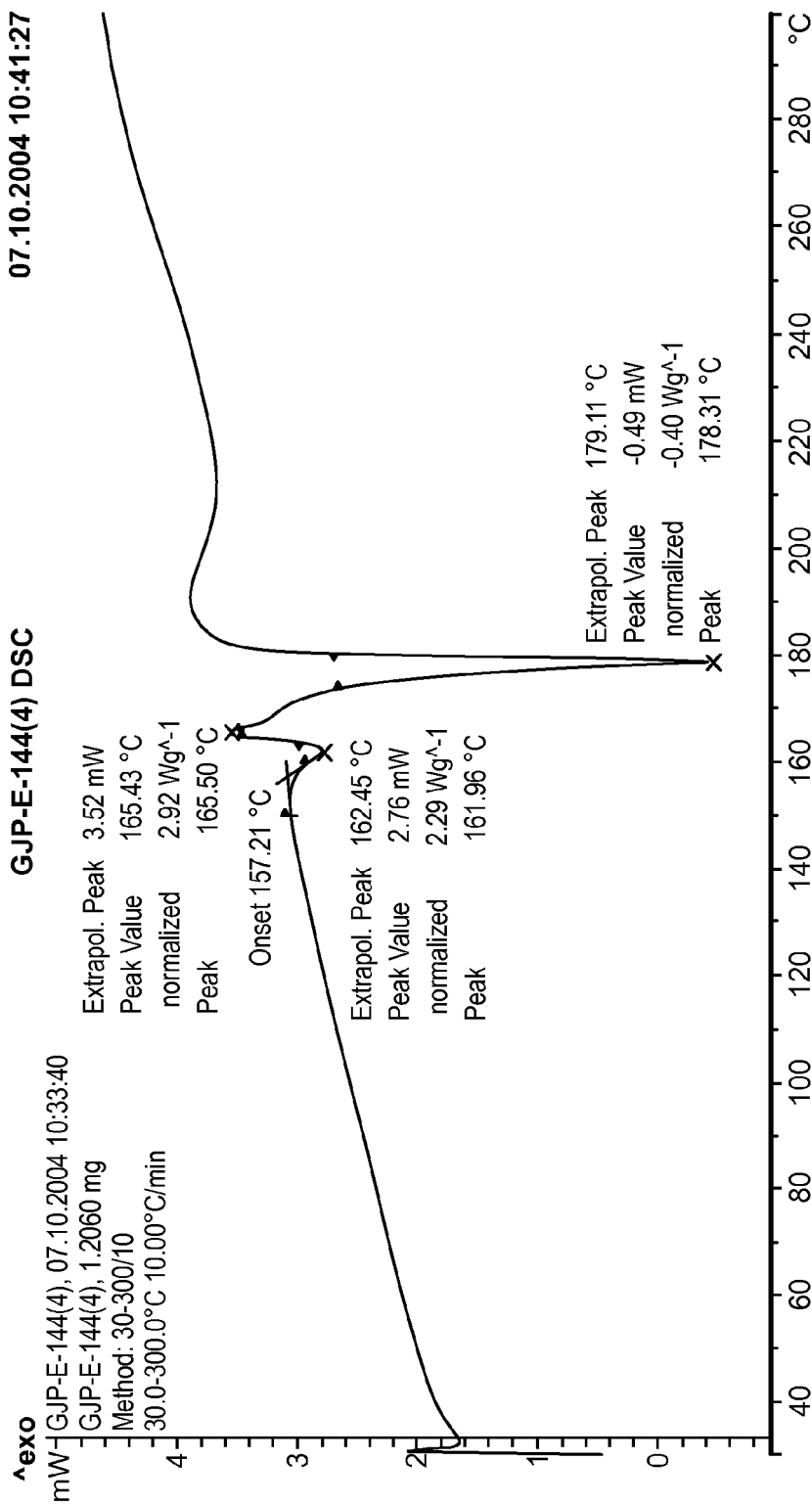
FIG. 7C depicts the DSC of this salt from DCM.

(E)-N-methyl-N-((3-methylbenzofuran-2-yl)methyl)-3-(7-oxo-5,6,7,8-tetrahydro-1,8-naphthyridin-3-yl) acrylamide p-toluene sulfonate Using method IIB, compound A, p-toluene sulfonic acid and THF as solvent, a solid crystallized during the cooling phase which was isolated as the title compound. The product showed a unique diffraction (XRPD) as compared to the free base as shown in FIG. 7A (high intensity peaks include those occurring at 6.5, 11.5, 12.25, 13.5, 14.5, 14.25, 15.5, 16, 18.5, 19, 26, and 27 2θ); mp 180.5° C. (DSC); $^1$H-NMR supports a ratio between compound and counter-ion of 1:1; no weight loss in TGA. The DCS of this salt from THF is depicted in FIG. 7B.

In a similar manner from DCM upon concentration (about half volume reduction), crystallization occurred to yield the title compound: unique XRPD; three thermal events in DSC, $^1$H-NMR supports an assignment with the ratio between compound A and counter-ion of 1:1.

Example 6

Figure 8:
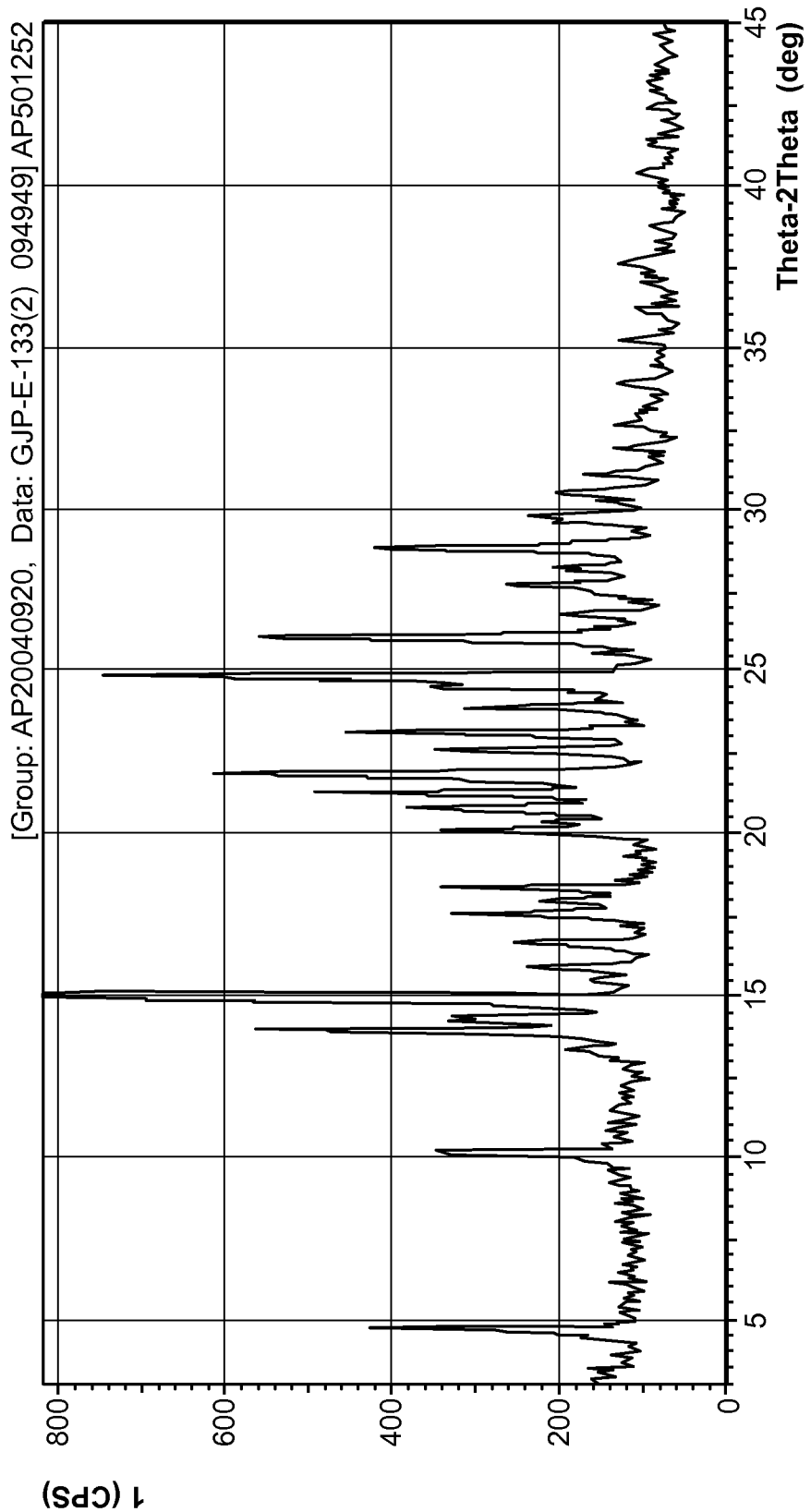
FIG. 8 depicts an XRPD spectra of a sulfate salt of (E)-N-methyl-N-((3-methylbenzofuran-2-yl)methyl)-3-(7-oxo-5,6,7,8-tetrahydro-1,8-naphthyridin-3-yl)acrylamide.

(E)-N-methyl-N-((3-methylbenzofuran-2-yl)methyl)-3-(7-oxo-5,6,7,8-tetrahydro-1,8-naphthyridin-3-yl)acrylamide sulfate Compound A, sulfuric acid and THF were processed as described in method IIB (Table 1) to yield the title compound as a crystalline solid. The product produced a unique XRPD pattern (FIG. 8) compared to the free-base as well as a different (lower) thermal event in the DSC. High intensity peaks include those occurring at 4.5, 10, 14.75, 14, 22, 24.5, and 26 2θ.

Example 7

(E)-N-methyl-N-((3-methylbenzofuran-2-yl)methyl)-3-(7-oxo-5,6,7,8-tetrahydro-1,8-naphthyridin-3-yl) acrylamide methane sulfonate Using general method III, described above, the title salt was prepared in a yield of 84.4% with analytical data consistent with those previously described for example 3: elemental analysis calculated for $C_{23}H_{26}N_3O_6 \cdot CH_3SO_3H$ as a monohydrate: C, 56.43; H, 5.56; N, 8.58. Found: C, 56.10; H, 5.38; N, 8.46.

Figure 9A:
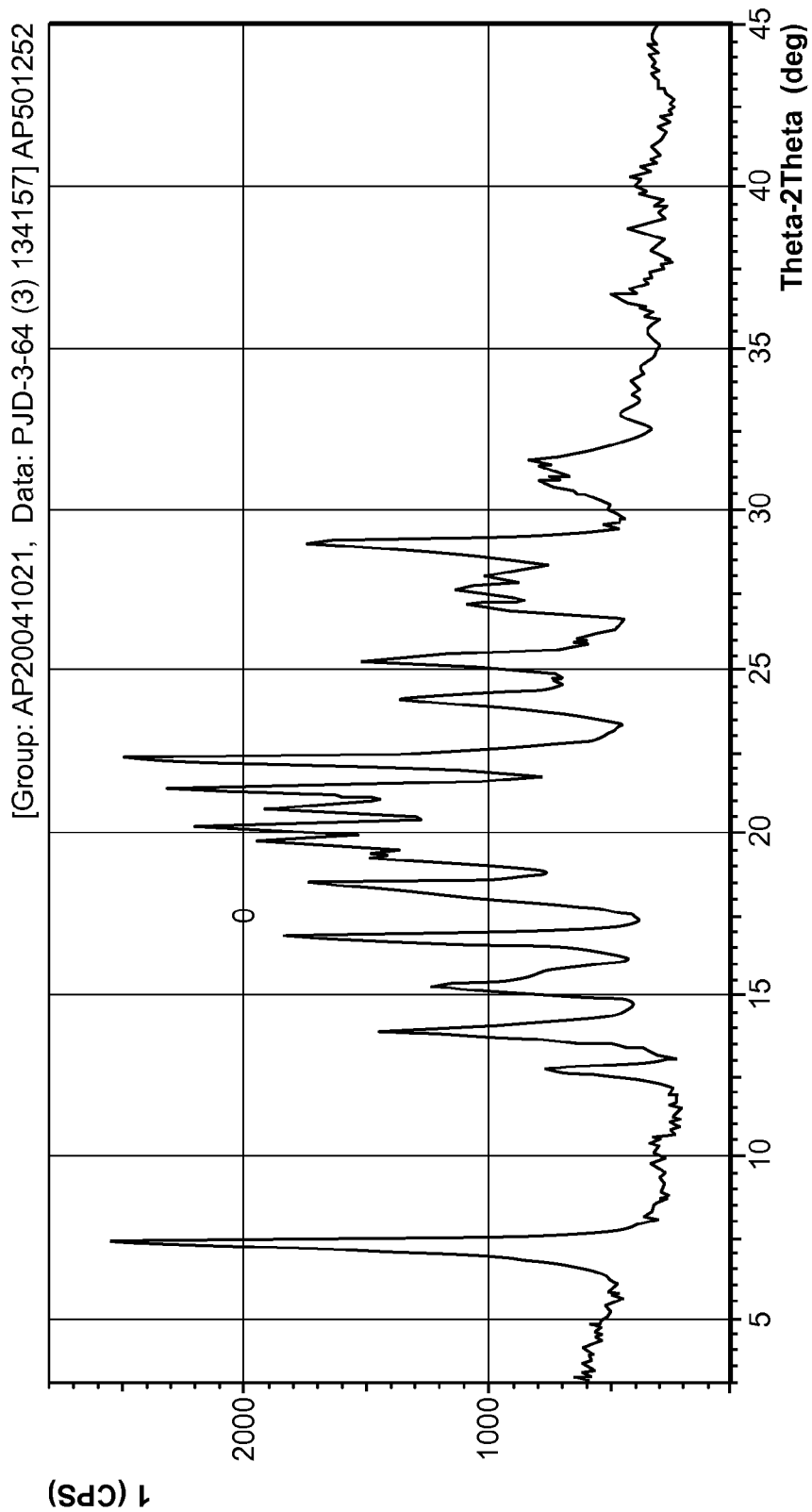
FIG. 9A depicts an XRPD spectra of a mesylate salt of (E)-N-methyl-N-((3-methylbenzofuran-2-yl)methyl)-3-(7-oxo-5,6,7,8-tetrahydro-1,8-naphthyridin-3-yl)acrylamide after ball milling
Figure 9B:
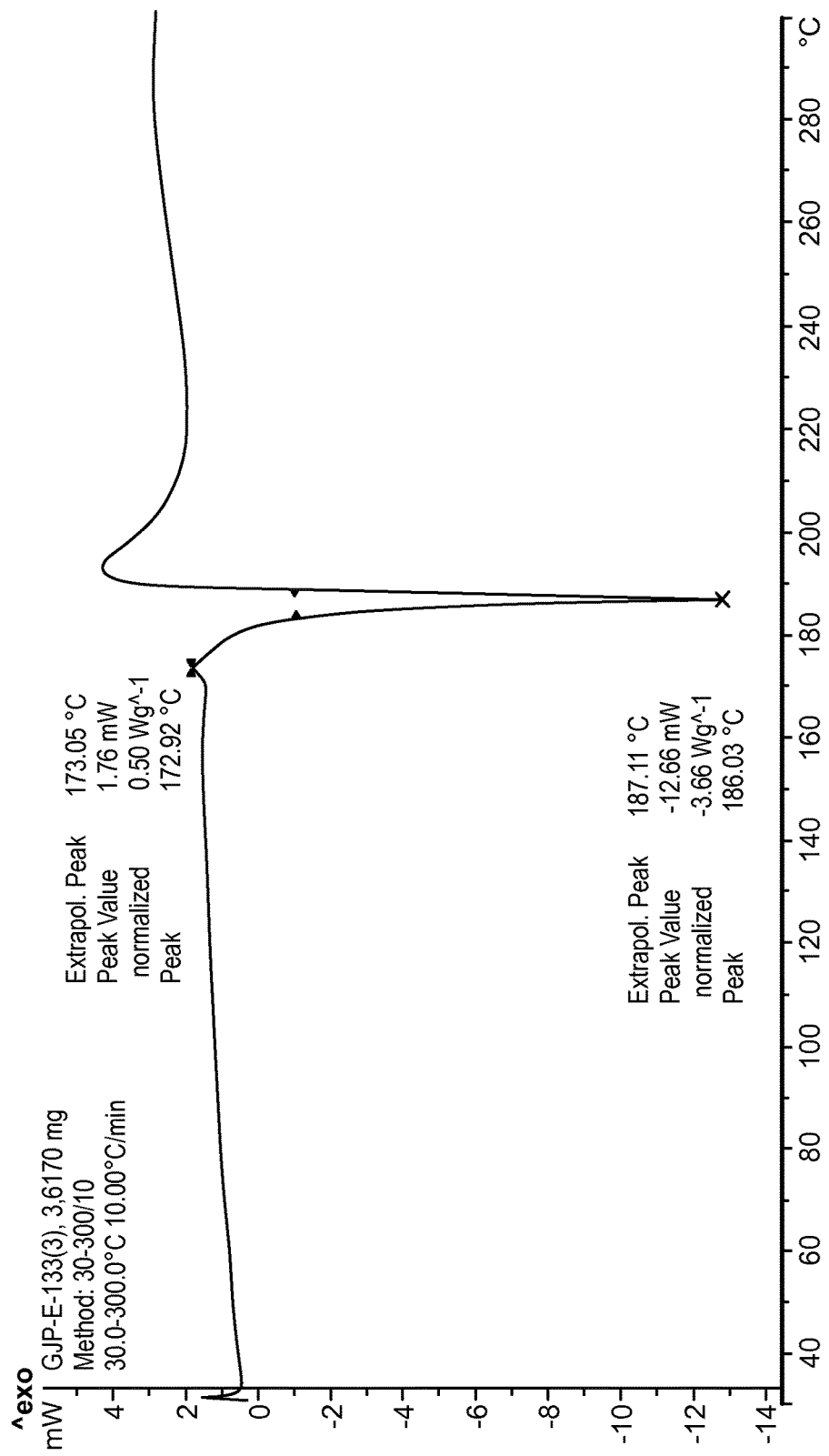
FIG. 9B depicts the DSC of this salt after ball milling.

A portion of this material was subjected to ball milling as described above; the XRPD shows crystalline material as depicted in FIG. 9A; DSC (FIG. 9B) shows one major thermal event and a decomposition exotherm.

Example 8

(E)-N-methyl-N-((3-methylbenzofuran-2-yl)methyl)-3-(7-oxo-5,6,7,8-tetrahydro-1,8-naphthyridin-3-yl)acrylamide p-toluene sulfonate Using general method III, described above, the title salt was prepared in a yield of 77.8% with analytical data consistent with those previously described for example 5: Analysis calculated for $C_{23}H_{26}N_3O_6$.p$CH_3$PhSOH: C, 63.60; H, 5.34; N, 7.67. Found: C, 63.31; H, 5.44; N, 7.56.

Figure 10A:
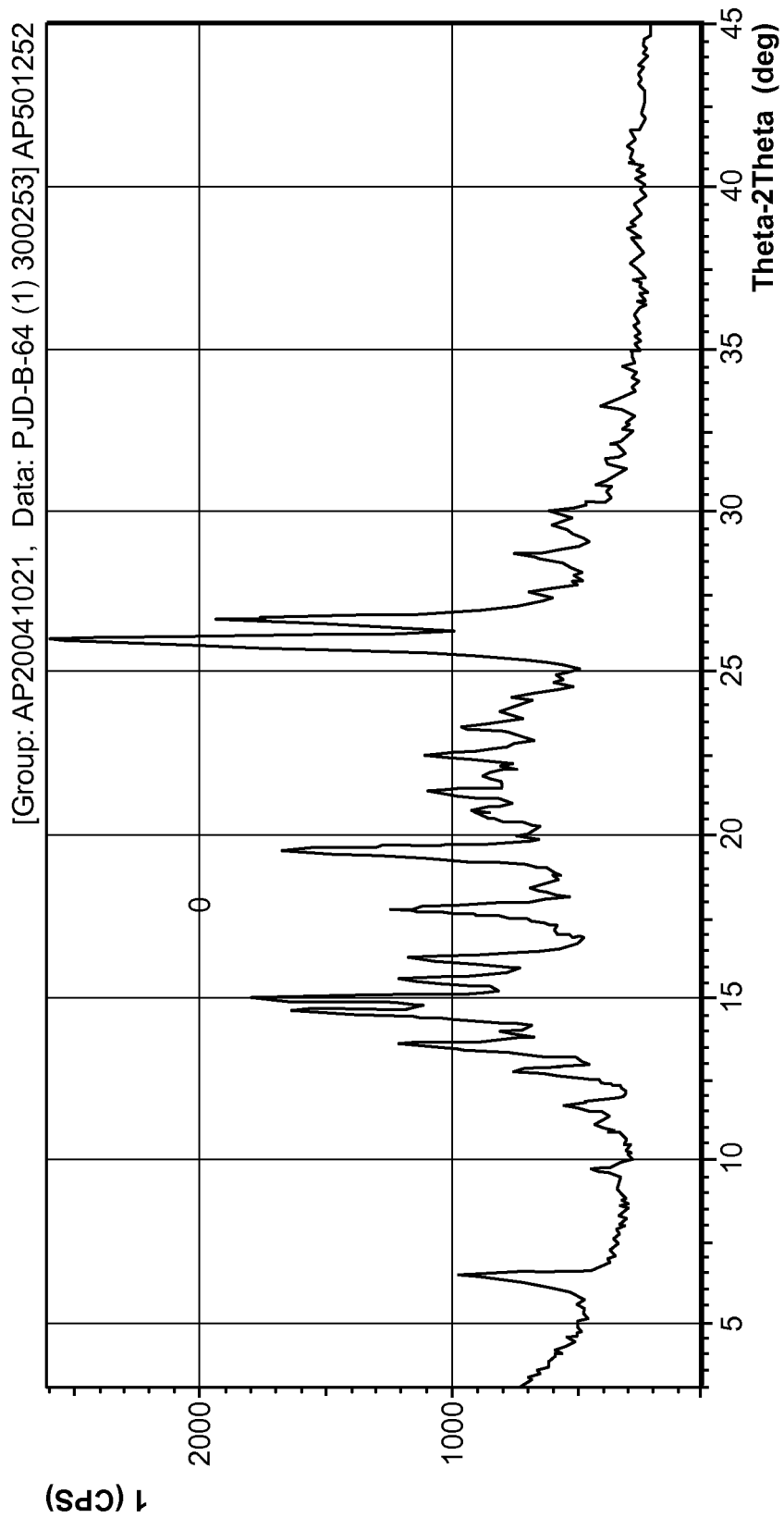
FIG. 10A depicts an XRPD spectra of p-toluenesulfonic salt of (E)-N-methyl-N-((3-methylbenzofuran-2-yl)methyl)-3-(7-oxo-5,6,7,8-tetrahydro-1,8-naphthyridin-3-yl)acrylamide after ball milling
Figure 10B:
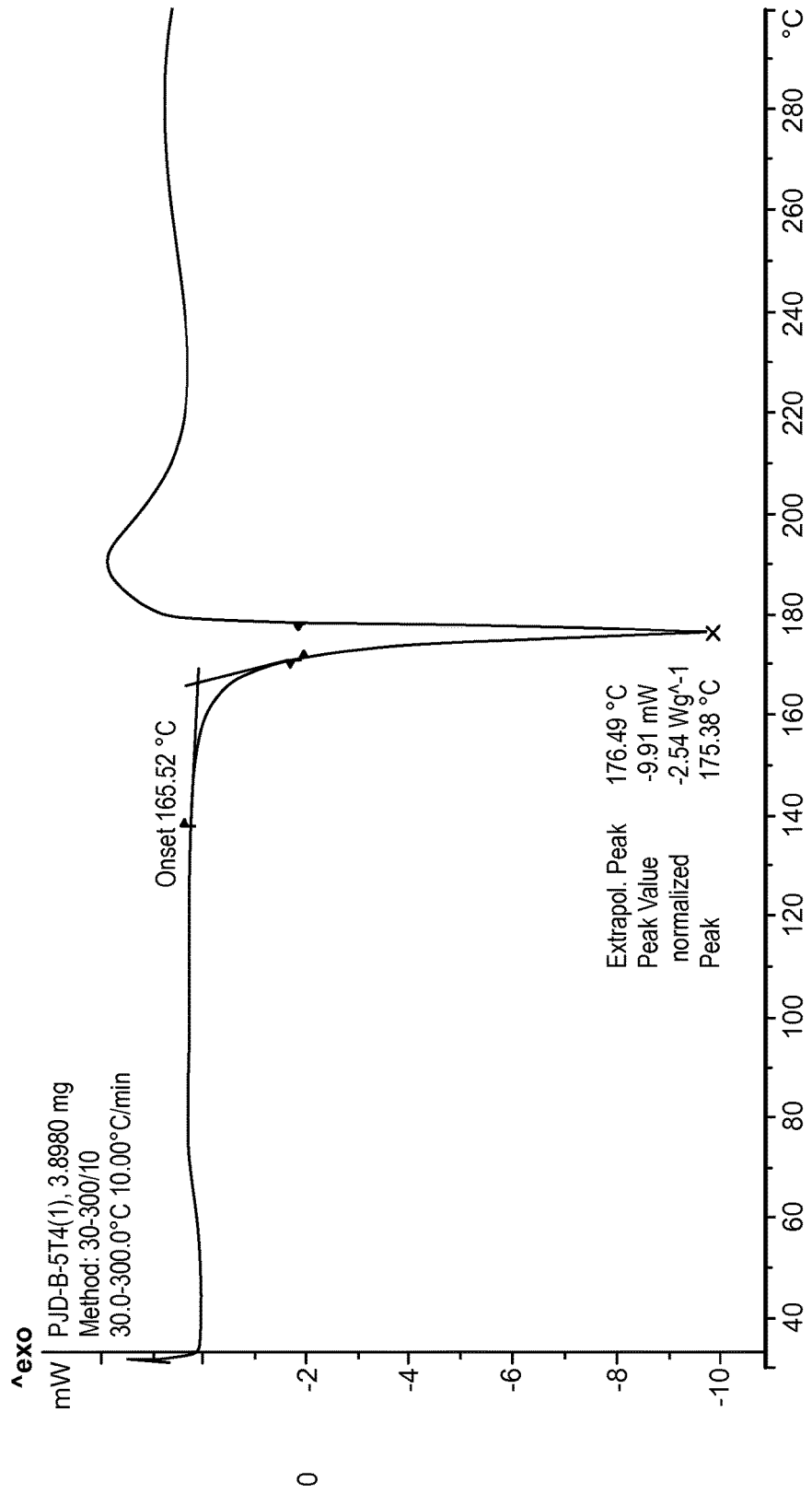
FIG. 10B depicts the DSC of this salt after ball milling.

A portion of this material was subjected to ball milling as described above: XRPD shows crystalline material as depicted in FIG. 10A; DSC (FIG. 10 B) shows one thermal event.

Example 9

Figure 11:
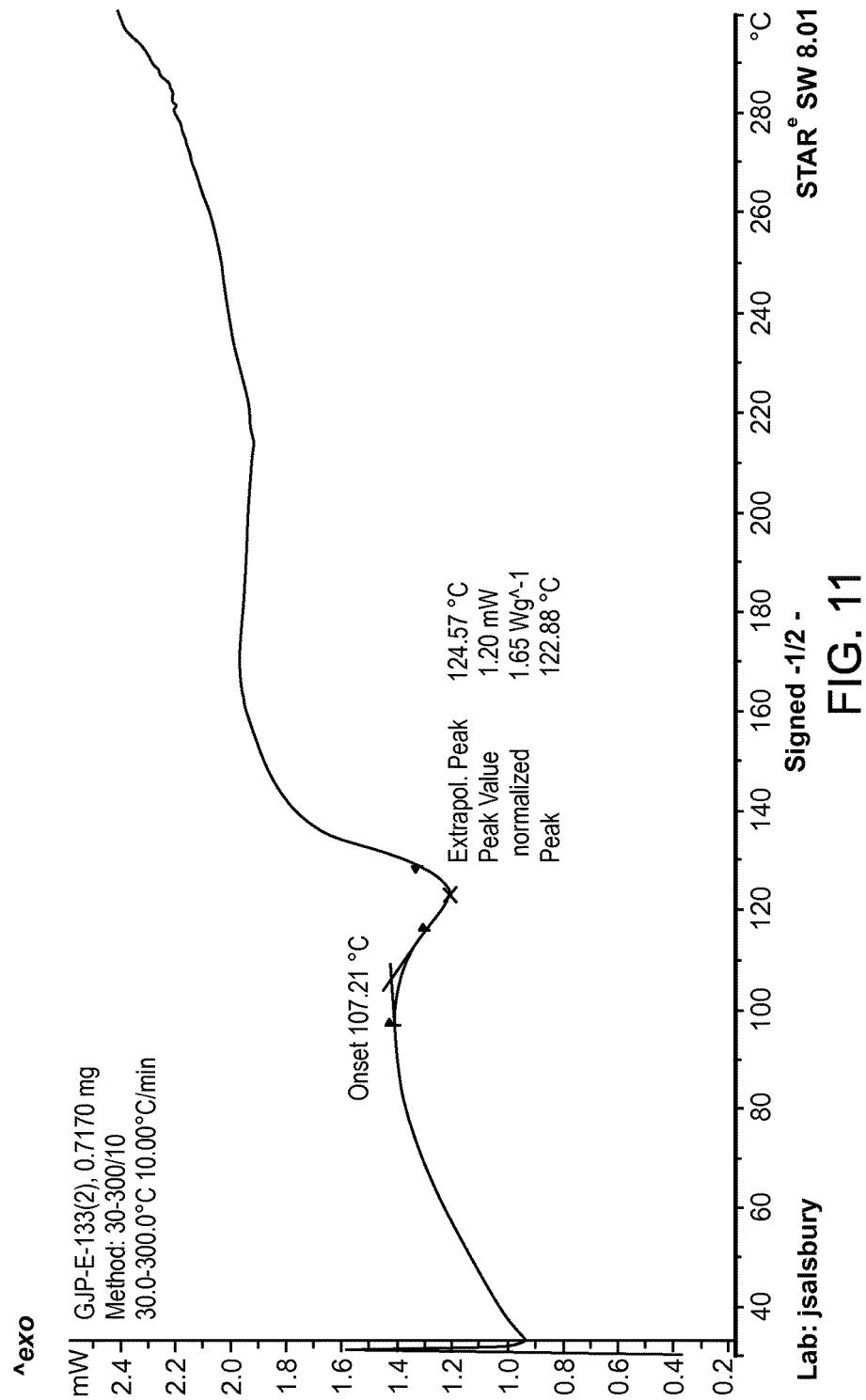
FIG. 11 depicts the DSC graph of (E)-N-methyl-N-((3-methylbenzofuran-2-yl)methyl)-3-(7-oxo-5,6,7,8-tetrahydro-1,8-naphthyridin-3-yl)acrylamide sulfate.

(E)-N-methyl-N-((3-methylbenzofuran-2-yl)methyl)-3-(7-oxo-5,6,7,8-tetrahydro-1,8-naphthyridin-3-yl)acrylamide sulfate Using method III, described above, the title salt was prepared in a yield of 84.4% with analytical data consistent with those previously described for example 6: Analysis calculated for $C_{23}H_{26}N_3O_6 \cdot H_2SO_4$: C, 55.80; H, 4.90; N, 8.87. Found: C, 56.00; H, 5.46; N, 7.87. The DSC is depicted in FIG. 11.

A portion of this material was subjected to ball milling as described above: XRPD shows amorphous material is obtained.

Example 10

(E)-N-methyl-N-((3-methylbenzofuran-2-yl)methyl)-3-(7-oxo-5,6,7,8-tetrahydro-1,8-naphthyridin-3-yl)acrylamide p-toluene sulfonate Monohydrate form: Large-scale process (Scheme II, vida supra)

A. N,3-dimethylbenzofuran-2-carboxamide

A mixture of 3-methylbenzofuran-2-carboxylic acid (1.0 kg, 5.676 mol) in methylene chloride (5.8 L) and DMF (5 mL) was chilled to ~2° C. A solution of oxalyl chloride (864 g, 6.81 mol) was added to the reaction mixture keeping the temperature below 10° C., over a period of 2 hrs. A vigorous evolution of a gas was observed. The reaction mixture was stirred overnight under nitrogen at room temperature and then refluxed for 3 hrs. All of the solids were dissolved to give a brown color solution. HPLC analysis of an aliquot indicated that the reaction was complete. The mixture was concentrated on a rotary evaporator and the residual oxalyl chloride was chased with DCM (2 L). The solid product was re-dissolved in DCM (6 L) in a round bottom flask (10 L) and chilled to ~-5° C. A solution of methyl amine (40% in water, 1.7 L, 3.5 eq, 19.86 mol) was carefully added to the acid chloride solution while keeping the temperature below 8° C. then stirred overnight at room temperature. Analysis of an aliquot indicated that the reaction was complete. Water (8.0 L) was added to the reaction mixture, the layers were separated, the aqueous layer was back extracted with DCM (2×3 L), the combined organic layer was washed with water (4 L) and dried over $Na_2SO_4$. The organic layer was filtered, the filtrate was concentrated and traces of DCM were co evaporated with heptanes (2 L). The heptanes slurry was filtered and the cake was washed with heptanes (2×2 L). All the brown color was removed in the heptane filtrate. The solid product was dried under high vacuum overnight to a constant weight. Yield of the title compound was 1.015 kg (94.5%). $^1$H NMR $\{CDCl_3\}$: δ (ppm) 8.45 (s, 1H), 7.61 (d, 1H), 7.41 (m, 2H), 7.30 (m, 1H), 3.03 (d, 2H), 2.63 (s, 3H). HPLC: 99.0 area % ($R_T$=7.91 min).

B. N-methyl-1-(3-methylbenzofuran-2-yl)methanamine

To a solution of THF (3.4 L) in a 22 L round bottom flask were carefully added lithium aluminum hydride pellets (261 g, 6.871 mol, 1.3 eq) and the mixture was stirred over night under a nitrogen atmosphere. Most of the pellets dissolved and a gray slurry formed. The mixture was chilled to 5° C. and a solution of N,3-dimethylbenzofuran-2-carboxamide (1.0 kg, 5.285 mol) in THF (7.7 L) was added carefully while maintaining the internal temperature below 10° C. The addition took ~1.5 hrs. Then the reaction mixture was carefully refluxed for 7 hrs and HPLC analysis at this stage indicated 85.9% of product, 13.9% of starting material and 1.2% of a side product. At this stage the heating was stopped, the heating mantle was replaced with a cooling bath and the mixture was cooled to −20° C. The reaction mixture was carefully quenched with water (330 mL) keeping the temperature below 0° C., followed by addition of an aqueous solution of 2 N NaOH (400 mL) and the resulting mixture was allowed to stand over night. A lot of greasy residue settled to the bottom the upper layer was turbid and was very difficult to filter. The THF layer was concentrated under vacuum and the residue was dissolved in ethyl acetate (4 L) and filtered (very slow filtration). The filter cake was washed with EtOAc (4×4 L) and the combined filtrate was concentrated on a rotary evaporator to obtain ~1.119 kg of crude oil. Total filtration time is about 2 days.

Similarly another 1.2 kg reaction (313 g of LAH) was completed and after work-up 1.5 kg of oil was isolated.

Purification of the combined crude oil by acid base work-up and silica gel chromatography yielded the title compound as a yellow oil (71.3%). $^1$H NMR $\{CDCl_3\}$: δ (ppm) 7.47 (d, 1H), 7.39 (d, 1H), 7.22 (m, 2H), 3.82 (s, 2H), 2.43 (s, 3H), 2.24 (s, 3H) HPLC: 98.3 area % ($R_T$=5.59 min).

C. (E)-tert-butyl 3-(7-oxo-5,6,7,8-tetrahydro-1,8-naphthyridin-3-yl)acrylate A 22-L three-necked round-bottomed flask with a mechanical stirrer, a thermocouple, a reflux condenser and a nitrogen inlet was flushed with $N_2$. The flask was charged with acetonitrile (8 L, 5 v), dimethylformamide (93.2 L, 2 v) and 6-bromo-3,4-dihydro-1,8-naphthyridin-2(1H)-one bromide (1.6 kg, 7.05 mol, 1 eq.). To the suspension were added diisopropylethylamine (1.33 kg, 10.57 mol, 1.5 eq.) and tert-butylacrylate (1.33 kg, 10.57 mol, 1.5 eq.). The suspension was then purged with a slow stream of $N_2$ for 10 min. Trio-tolylphosphine (0.214 kg, 0.705 mol, 0.1 eq) and palladium diacetate (0.079 kg, 0.352 mol, 0.05 eq) were added to the reaction mixture. The reaction mixture was heated to 75-80° C. and stirred at 75-80° C. for 20 h. The reaction mixture was cooled to 20-25° C., diluted with water (10 v) and stirred for one hour. The solid was collected by vacuum filtration using a Buchnner funnel with a cloth filter and 20-L glass receiver flask. The solids were then washed with water (3×1 v) followed by heptane (2×1 v). The light brown damp solid was dried under vacuum at 30-35° C. with a slow $N_2$ bleed for 48 h to a constant weight to give 2.11 kg of light brown solid. This solid was then suspended DCM/MeOH (10 v/1 v) under $N_2$ in two 22-L three necked RBFs with a mechanical stirrer, a thermocouple and a reflux condenser. To each of these RBFs charcoal (100 g, ALDRICH Activated Darco G 60-100 mesh) was added and the mixture allowed to stir at 20-25° C. for 20 h. The suspensions were filter through a pad of celite (500 g)/silica gel (500 g) using a cintered glass funnel and a 20-L glass filter flask. The solid cake was rinsed with DCM (3×1 v). The combined filtrate was concentrated under vacuum ~30-35° C. and the residue was diluted with heptane/ethyl acetate (3 v/3 v) and further concentrated to a suspension. The solid product was collected under vacuum by filtration using a Buchnner funnel with a cloth filter. The solids were rinsed with heptane (3×1.25 v) and the damp solid was dried under vacuum at 30-35° C. with a slow $N_2$ bleed for 90 h to a constant weight to give 1.58 kg (82%) of the desired product as a yellow solid.

$^1$H NMR {DMSO (d$_6$)}: δ (ppm) 10.63 (br, 1H, NH), 8.36 (s, 1H, CH), 8.01 (s, 1H, CH), 7.52 (d, J=15.6 Hz, 1H, CH), 6.51 (d, J=15.6, Hz, 1H, CH), 2.93 (t, J=7.9 Hz, 2H, CH$_2$), 2.56 (t, J=7.9 Hz, 2H, CH$_2$), 1.51 (s, 9H, C(CH$_3$)$_3$).

$^{13}$C NMR {DMSO (d$_6$)}: δ (ppm) 171.4 (C), 165.9 (C), 153.3, 147.8, 140.7, 134.2, 125.1, 119.5, 119.4, 80.3 (C), 30.4 (CH$_2$), 28.3 (CH$_3$) & 23.7 (CH$_2$).

HPLC: 98.0 area % (R$_T$=11.52 min).

D. (E)-3-(7-oxo-5,6,7,8-tetrahydro-1,8-naphthyridin-3-yl)acrylic acid

A 22-L three-necked round-bottomed flask with a mechanical stirrer, a thermocouple, a reflux condenser and a nitrogen inlet was flushed with $N_2$ then charged with glacial acetic acid (12.5 L, 7 v) and (E)-tert-butyl 3-(7-oxo-5,6,7,8-tetrahydro-1,8-naphthyridin-3-yl)acrylate (1.58 kg, 5.76 mol, 1.0 eq.). To the yellow suspension, HBr (2.91 kg, 17.28 mol, 3 eq., 48% aq.) was added. The resulting suspension was stirred at 20-25° C. Due to difficulty of stirring, acetic acid (7.5 L) was added. After stirring for 2.5 h, ~1 mL of yellow suspension was taken out, filtered, washed with ethyl acetate and dried. The dry solid dissolved in CDCl$_3$ and the progress of the reaction was monitored by $^1$H NMR. The result indicated >90% reaction completion. After another 16 hours of stirring at the same temperature, the $^1$H NMR analysis indicated the reaction was complete. The solid was collected by filtration using a Buchnner funnel with a cloth filter (WHATMAN PAPER Cat#1821915) and 20-L glass receiver under vacuum. The solids were washed with ethyl acetate (2×2 v). The damp solid was transferred into a 20-L plastic bucket containing ethyl acetate (12 L, 8 v) and agitated with a mechanical stirred. The resulting suspension was stirred at 20-25° C. for 24 h. Solid was collected by filtration using a Buchnner funnel with a cloth filter and 20-L glass receiver under vacuum. The solids were washed with ethyl acetate (3×2 V) and the damp solid was dried under vacuum at 30-35° C. with a slow $N_2$ bleed for 60 h to a constant weight to give 1.60 kg of the HBr salt of the desired product as a yellow solid.

$^1$H NMR {DMSO (d$_6$)}: δ (ppm) 10.4-10.8 (br, 2H, HBr, NH), 8.36 (s, 1H, CH), 8.01 (s, 1H, CH), 7.55 (d, J=16.2 Hz, 1H, CH), 6.51 (d, J=16.2, Hz, 1H, CH), 2.93 (t, J=7.2 Hz, 2H, CH$_2$), 2.56 (t, J=7.2 Hz, 2H, CH$_2$), 1.51 (s, 9H, C(CH$_3$)$_3$).

$^{13}$C NMR {DMSO (d$_6$)}: δ (ppm) 171.5 (C), 167.9 (C), 153.0, 147.1, 140.1, 134.8, 125.3, 120.1, 119.2, 30.4 (CH$_2$), & 23.8 (CH$_2$).

HPLC: 99.6 area % (R$_T$=6.70 min).

E. (E)-N-methyl-N-((3-methylbenzofuran-2-yl)methyl)-3-(7-oxo-5,6,7,8-tetrahydro-1,8-naphthyridin-3-yl)acrylamide A 22-L three-necked round-bottomed flask with a mechanical stirrer, a thermocouple, a reflux condenser and a nitrogen inlet was flushed with $N_2$. The flask was charged with DMF (7.5 L, 5 v) and (E)-3-(7-oxo-5,6,7,8-tetrahydro-1,8-naphthyridin-3-yl)acrylic acid (1.49 kg, 4.98 mol, 1.0 eq.). To the yellow suspension, HOBT (0.74 kg, 5.48 mol, 1.1 eq.), EDCI (1.15 kg, 5.98 mol, 1.2 eq) and N-methyl-1-(3-methylbenzofuran-2-yl)methanamine (0.96 kg, 5.48 mol, 1.1 eq) were added. During the addition an exotherm was observed and the temperature increased from 20.3° C. to 36.4° C. To the resulting thick suspension was added DIPEA (1.93 kg, 14.94 mol, 3 eq.) and an exotherm was observed to 41.9° C. During the addition the suspension changed to a clear brown solution. The resulting solution was stirred at 38-42° C. After about 45 min a new solid started to form. After stirring for 1.5 h, ~1 mL of suspension was taken, the progress of the reaction was monitored by HPLC and the results indicated >95% reaction completion. After another 16 hours of stirring at the same temperature, $^1$H NMR and HPLC analysis indicated the reaction was complete. Half of the reaction mixture was transferred to another 22-L three-necked round-bottomed flask containing a mechanical stirrer, a thermocouple, a reflux condenser and a nitrogen inlet. The contents of both flasks were allowed to cool to 20-25° C. and each reaction mixture was diluted with H$_2$O (8 L, 5.3 v) over 15 min. Both reaction mixtures showed an exotherm during the water addition to 30-35° C. The resulting suspensions were allowed to stir at 20-25° C. for 3.5 h. Solid was collected by filtration using a Buchnner funnel with a cloth filter and 20-L glass receiver under vacuum. The solids were washed with water (4×1.4 v), heptane (1×1.4 v) and ethyl acetate (3×1 v). The damp solid was dried under vacuum at 30-35° C. with a slow $N_2$ bleed for 120 h to a constant weight to give 1.67 kg of the title compound as yellow solid. The material was analyzed indicating 98.48 area % HPLC purity with 146 ppm residual Pd.

A 22-L three-necked round-bottomed flask with a mechanical stirrer, a thermocouple, a reflux condenser and a nitrogen inlet was flushed with $N_2$. The flask was charged with DMF (7 L, 4 v) and a portion of the crude product from above (1.65 kg, 4.98 mol, 1.0 eq.). To the resulting thick suspension was added DIPEA (1 L, 0.75 v.). The suspension was heated to 52-57° C. and stirred at the same temperature. After 20 hours of stirring at 52-57° C. the suspension was allowed to cool to 20-25° C. Solid was collected by filtration using a Buchnner funnel with a cloth filter and 20-L glass receiver under vacuum. The solids were washed with DMF (2×0.7 v), H$_2$O (3×2 v) and methanol (2×2 v). The damp solid was dried under vacuum at 30-35° C. with a slow $N_2$ bleed for 110 h to a constant weight to give 1.56 kg of the desired product as a yellow solid. The material was analyzed and the results indicated 99 area % HPLC purity with 20 ppm Pd. A 0.75 kg of this material was used for the salt formation and the remaining 0.813 kg was subjected to the procedure as described above beginning with suspension in DMF. A 0.78 kg portion of desired product was isolated as solid in 95% yield with 99.0 area % HPLC purity with 14 ppm of residual Pd. This material was used for subsequent milling (Micron technologies).

$^1$H NMR {DMSO (d$_6$)}: δ (ppm) 10.69 (br, H, NH), 8.38 (two s, 1H, CH), 8.09 (two s, 1H, CH), 7.48-7.58 (m, 3.4H), 7.19-7.31 (m, 2.5H), 5.01 (s, 0.8H), 4.80 (s, 1.2H), 3.37 (s, 0.4H), 3.20 (s, 1.6H) 2.89-2.94 (m, 2H), 2.50-2.94 (m, 5H, CH$_2$, CH$_3$), 2.27 (s, 3H, CH$_3$).

$^{13}$C NMR {DMSO (d$_6$)}: δ (ppm) 171.5 (C), 165.9 (C), 154.0, 152.9, 149.8, 147.7, 139.2, 138.8, 134.2, 126.1, 125.0, 124.8, 122.9, 120.0, 119.5, 118.0, 111.3, 42.4 (CH$_2$), 35.4 (CH$_3$), 30.5 (CH$_2$), 23.8 (CH$_2$) & 8.0 (CH$_3$).

DSC: 245.4° C.
TGA: 0.2652 @ 240° C.
HPLC: 99.7 area % (R$_T$=11.52 min)
LC-MS: 376 amu (MW. 376.17)
KF: 0.23%
Pd: 16 ppm
Heavy Metals: <20 ppm
Residue on Ignition: 0.16%
C$_{21}$H$_{22}$N$_3$O$_3$: Calcd. C, 70.38%; H, 5.64%; N, 11.19%.
Found C, 70.08%; H, 5.57%; N, 11.17%.

F. (E)-N-methyl-N-((3-methylbenzofuran-2-yl)methyl)-3-(7-oxo-5,6,7,8-tetrahydro-1,8-naphthyridin-3-yl)acrylamide Tosylate Monohydrate A 22-L three-necked round-bottomed flask with a mechanical stirrer, a thermocouple, a reflux condenser and a nitrogen inlet was flushed with N$_2$. The flask was charged with DCM (12 L, 16 v) and (E)-N-methyl-N-((3-methylbenzofuran-2-yl)methyl)-3-(7-oxo-5,6,7,8-tetrahydro-1,8-naphthyridin-3-yl)acrylamide (0.75 kg, 1.999 mol, 1.0 eq.). To the suspension, MeOH (1 L, 1.33 eq) was added and resulting suspension was heated to IT=35-40° C. When IT=35° C., a solution of TsOH.H$_2$O (0.38 kg, 1.999 mol. 1 eq.) in methanol (0.5 L, 0.67 v) was added over 10 min while maintaining IT=35-40° C. After the addition was complete a clear solution was formed which was then filtered through 0.45 μm filter paper. The filtrate was divided in to two halves and transferred into two 22-L three-necked round-bottomed flasks with a mechanical stirrer, a thermocouple, a reflux condenser and a nitrogen inlet. Each solution was stirred at IT=35-40° C. and water (32 g, 2 mol, 1 eq.) was added. The clear solutions were then diluted with heptane (6 L, 8 v) over 15 min while maintaining IT=35-40° C. The resulting suspensions were allowed cooled to IT=20-25° C. over 3 h and allowed to stir at the same temperature for 18 h. The solid was collected by filtration using a Buchnner funnel with a cloth filter and 20-L glass receiver under vacuum. The solids were washed with heptane (3×2.7 v). The damp solid was dried under vacuum at 30-35° C. with a slow N$_2$ bleed for 72 h to a constant weight to give 1.06 kg of the desired product as a white solid. The material was analyzed and the results indicated 98.3% area HPLC purity with 7.7 ppm Pd. This material was used for ball milling.

$^1$H NMR {DMSO (d$_6$)}: δ (ppm) 10.80 (br, H, NH), 8.38 (two s, 1H, CH), 8.16 (two s, 1H, CH), 7.48-7.58 (m, 5.4H), 7.21-7.28 (m, 2.5H), 7.13 (d, J=7.8 Hz, 2H, CH), 6.80 (br, 3H, TsOH, H$_2$O), 5.0 (s, 0.8H), 4.80 (s, 1.2H), 3.20 (s, 1.6H) 2.91-2.96 (m, 2.4H), 2.50-2.94 (m, 5H), 2.29 (s, 3H, CH$_3$), 2.27 (s, 3H, CH$_3$).

$^{13}$C NMR {DMSO (d$_6$)}: δ (ppm) 171.5 (C), 165.9 (C), 154.0, 152.9, 149.8, 147.7, 139.2, 138.8, 134.2, 128.8, 126.3, 126.1, 125.0, 124.8, 122.9, 120.0, 119.5, 118.0, 111.3, 42.4 (CH$_2$), 39.2 (CH$_3$), 30.5 (CH$_2$), 23.8 (CH$_2$), 21.3 (CH$_3$) & 8.0 (CH$_3$).

DSC: 176.1° C.
TGA: 0.2652 @ 240° C.
HPLC: 98.3% area (R$_T$=11.52 min)
LC-MS: 376 amu (MW. 376.17)
KF: 3.72%
Pd: 6.5 ppm
Heavy Metals: <20 ppm
Residue on Ignition: 0.1%
C$_{28}$H$_{32}$N$_3$O$_7$: Calcd. C, 61.58%; H, 5.52%; N, 7.43%.
Found C, 61.49%; H, 5.53%; N, 7.46%.

Figure 12:
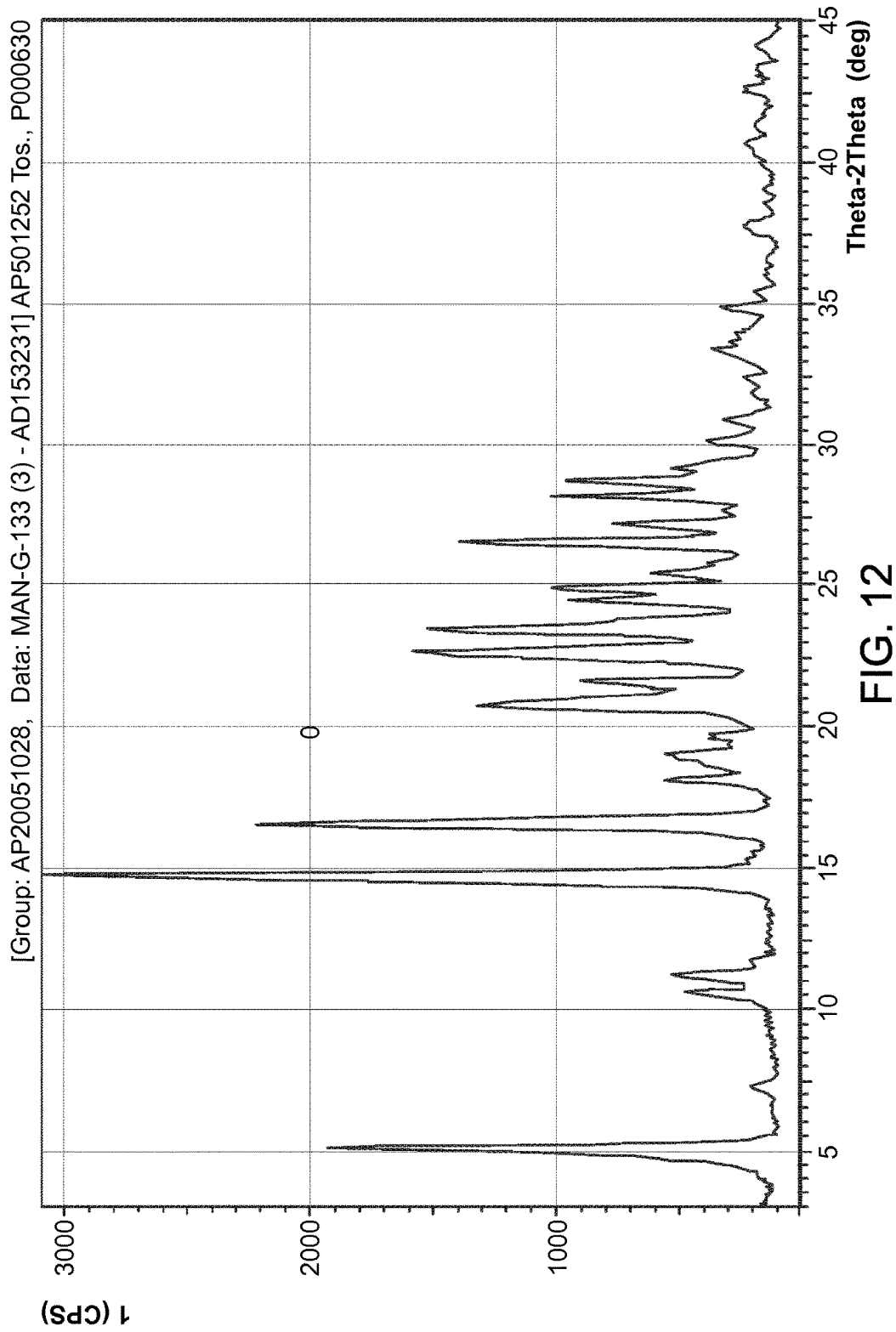
FIG. 12 depicts an XRPD spectra of a p-toluenesulfonic salt monohydrate of (E)-N-methyl-N-((3-methylbenzofuran-2-yl)methyl)-3-(7-oxo-5,6,7,8-tetrahydro-1,8-naphthyridin-3-yl)acrylamide.

The resulting solid was filtered to collect the title compound; XPRD of title compound depicted in FIG. 12. High intensity peaks include those occurring at 5, 10.5, 11.25, 14.5, 16.5, 18, 19, 19.5 and 22.5 2θ.

Example 12: (E)-N-methyl-N-((3-methylbenzofuran-2-yl)methyl)-3-(7-oxo-5,6,7,8-tetrahydro-1,8-naphthyridin-3-yl)acrylamide Tosylate (Anhydrate): Large-scale process The reaction forming the title compound can be processed in multiple, e.g. eleven 150-g batches and one 25-g batch, and combined during the final filtration. Described below is a representative 150-g run.

A 72-L, four-neck, round-bottom flask was equipped with a reflux condenser, an overhead, mechanical stirrer, a temperature probe with a temperature controller, and a nitrogen inlet adapter. The reactor was charged with (E)-N-methyl-N-((3-methylbenzofuran-2-yl)methyl)-3-(7-oxo-5,6,7,8-tetrahydro-1,8-naphthyridin-3-yl)acryl-amide, prepared as described in Example 10E, (150 g) and tetrahydrofuran (40 kg). The reaction mixture was heated to 60° C. to partially dissolve API. p-Toluenesulfonic acid (80 g, 0.42 mol) was added to the reactor as a solution in tetrahydrofuran (400 mL). The reaction was aged for 1 h at 60° C. Heptane (10 kg) was then added and the internal temperature decreased to 51° C. The reaction mixture was heated back to 60° C. and then allowed to cool to ambient temperature overnight. The white solid was collected via filtration through Sharkskin filter paper and combined with all other runs affording 3377 g of wet solid. The solid was dried at 50° C. in a vacuum oven for 48 h and combined with ten additional 150-g batches and one 25-g batch to afford 2119.3 g of product. The solid was then milled in 12-g batches using a Fritsch Pulverisette 6-ball mill in a 240-mL bowl with 150 agate balls at 200 rpm for 1 min. The milled product was then blended in a large beaker affording 2134 g of product (87%). The $^1$H NMR and $^{13}$C NMR spectra of the product were consistent with the assigned structure. ESI MS: m/z 376 [C$_{22}$H$_{21}$N$_3$O$_3$+H]+. HPLC analysis (Method A): 98.8% (AUC), t$_R$=13.1 min. XRPD spectra depicted in FIG. 13.

Example 13 (Z)—N-methyl-N-((3-methylbenzofuran-2-yl)methyl)-3-(7-oxo-5,6,7,8-tetrahydro-1,8-naphthyridin-3-yl)acrylamide Scheme IV depicts one route to a cis-isomer of Compound A:

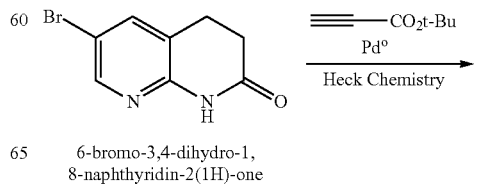

Scheme IV 6-bromo-3,4-dihydro-1,8-naphthyridin-2(1H)-one

43

-continued

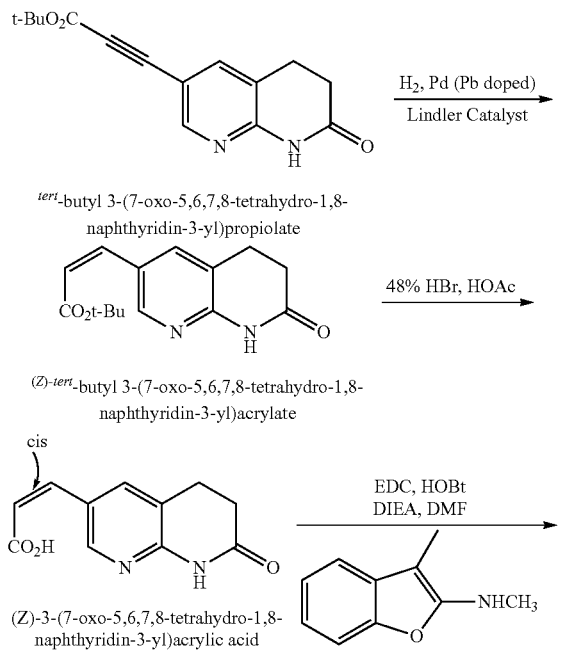

*tert*-butyl 3-(7-oxo-5,6,7,8-tetrahydro-1,8-naphthyridin-3-yl)propiolate (Z)-*tert*-butyl 3-(7-oxo-5,6,7,8-tetrahydro-1,8-naphthyridin-3-yl)acrylate (Z)-3-(7-oxo-5,6,7,8-tetrahydro-1,8-naphthyridin-3-yl)acrylic acid

44

-continued

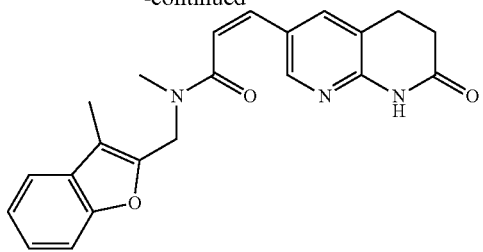

(Z)-N-methyl-N-((3-methylbenzofuran-2-yl)methyl)-3-(7-oxo-5,6,7,8-tetrahydro-1,8-naphthyridin-3-yl) acrylamide
Cis-isomer, MW 375.42

Example 14 Pharmocokinetic Studies

Male rats were used for the study of both milled and unmilled salt forms of Compound A and compared to the free base (i.e. compound A). All drug forms were dosed in the same vehicle (80% PEG400). Table 3 reports the pharmacokinetic parameters of Compound A and its mesylate and tosylate salts in male rats following a single oral dose in 80% PEG400. Drug exposure, as measured by Cmax or AUC, of the milled drug and the various salt forms increased by 3 to 8 fold when compared to the free base unmilled form.

TABLE 3

| Study_no | Batch | Salt | Particle state | Dose (mg/kg) | Cmax (ng/ml) | AUClast (ng*hr/ml) | Half life (hr) | AUCinf (ng*hr/ml) |
|---|---|---|---|---|---|---|---|---|
| 460180 | 4 | Free base | Unmilled | 30 | 421 | 1159 | 2.0 | 1255 |
| 460266 | 9 | Free base | Milled | 30 | 1974 | 6370 | 5.5 | 6568 |
| 460266 | 10 | Sulfate | Unmilled | 30 | 1940 | 9477 | 5.7 | 9966 |
| 460266 | 11 | Tosylate | Milled | 30 | 1613 | 9455 | 3.5 | 9509 |
| 460266 | 12 | Mesylate | Milled | 30 | 884 | 5769 | 5.0 | 6039 |

Example 15 Solubility in Cyclodextrins

An intravenous formulation and solubility study was conducted to compare milled free base (Compound A) and the milled tosylate monohydrate salt of Compound A in cyclodextrins. The solubilities are shown in Table 4. At cyclodextrin concentrations of 10%, the solubility of the tosylate monohydrate of Compound A milled was approximately 10 fold higher that the free base milled form in sulfobutyl ether beta-cyclodextrin. The overall results suggest a dual mechanism of solubilization including both complexation with the cyclodextrin core and ion pair formation afforded by the tosylate salt form and not by the free base.

TABLE 4

| | | Solubility (µg/ml) in: | |
|---|---|---|---|
| Drug form | Cyclodextrin concentration (%) | Hydroxypropyl Beta-Cyclodextrin | Sulfobutyl Ether Beta-Cyclodextrin |
| Free base milled | 10 | $9^a$-$20^b$ | 7 |
| Tosylate monohydrate milled | 10 | 26 | 67 |
| Free base milled | 40 | Not determined | Not determined |
| Tosylate monohydrate milled | 40 | 370 | 4003 |

[a]Procedure consisted of evaporating an ethanol/water/DMA blend of the cyclodextrin and API and reconstituting with water
[b]Shake-flask technique Example 16 Mouse Infection Model Compound A (free base) unmilled, and the tosylate salt of Compound A milled were tested in the same mouse thigh abscess model following single oral doses in 0.5% carboxymethyl cellulose. Mice (6 per dosing group) were rendered neutropentic, and the thigh of each mouse was injected with $1\times10^5$ colony forming units (CFU) of *Staphylococcus aureus* ATCC 29213. Two hours post infection, mice were dosed with the drug orally, and at 6 hours post dose, bacterial viable counts where determined from the thighs of all the mice. Efficacy was calculated as the average change in CFU/thigh compared to time 0 (time of dosing) controls. The results are presented in Table 5.

TABLE 5

| Oral Dose (mg/kg) | Study number HH-018 Average Change logCFU/thigh | | Study number HH-023 Average Change logCFU/thigh | |
|---|---|---|---|---|
| | Free base unmilled | SD | Tosylate milled | SD |
| 0 | 1.74 | 0.37 | 2.1 | 0.33 |
| 0.3 | 1.6 | 0.08 | 1.31 | 1.89 |
| 1 | 1.35 | 0.16 | 1.08 | 0.25 |
| 3 | 0.3 | 0.67 | −0.42 | 0.19 |
| 10 | 0.36 | 0.65 | −0.62 | 0.5 |
| 30 | −0.29 | 0.06 | −0.77 | 0.78 |

Figure 14:
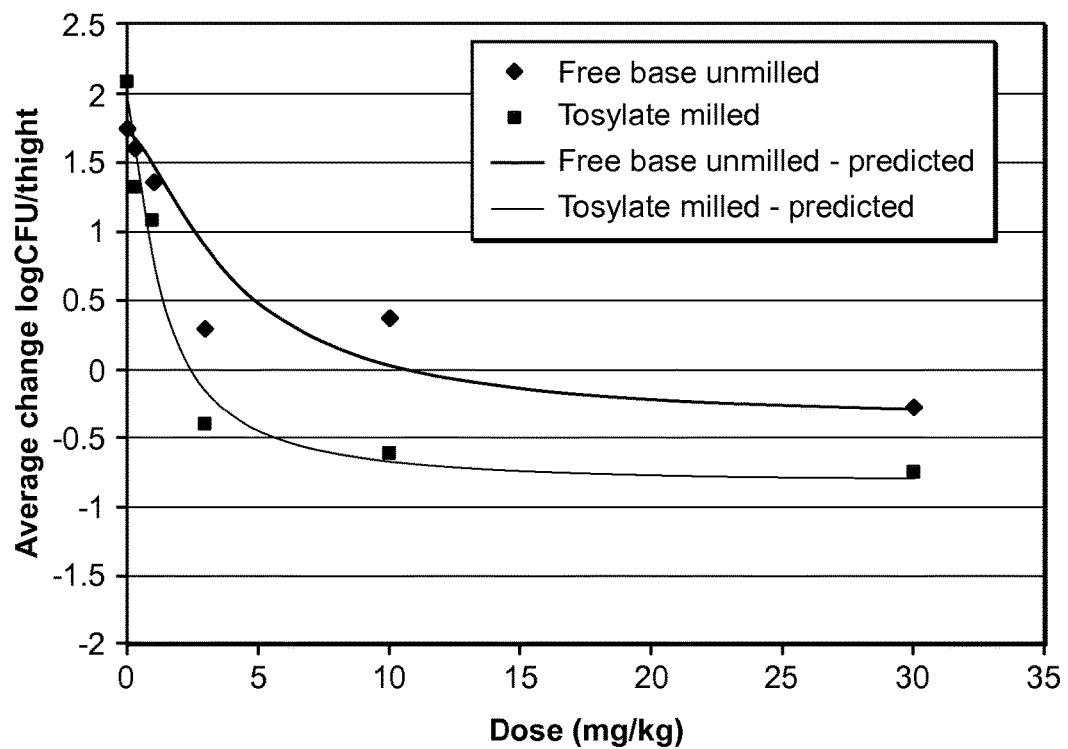
FIG. 14 depicts the oral efficacy of the tosylate salt of (E)-N-methyl-N-((3-methylbenzofuran-2-yl)methyl)-3-(7-oxo-5,6,7,8-tetrahydro-1,8-naphthyridin-3-yl)acrylamide in comparison to the free base form of (E)-N-methyl-N-((3- methylbenzofuran-2-yl)methyl)-3-(7-oxo-5,6,7,8-tetra-hydro-1,8-naphthyridin-3-yl)acrylamide in a mouse thigh abscess model.

These data were then fitted with a standard Inhibitory Effect Sigmoid Emax Model using WinNonLin v. 5.1, and the results are shown in Table 6 and FIG. 14. The results show that the milled tosylate salt form was 3 to 4 times more efficacious than the free base unmilled form as seen in the static dose (dose required to reach 50% (ED50) and 80% (ED80) efficacy). This result is consistent with the increased exposure of the tosylate milled form vs. the free base unmilled form in the pharmacokinetic study (Table 3).

TABLE 6

| Drug form | Static dose (mg/kg) | ED50 (mg/kg) | ED80 (mg/kg) |
|---|---|---|---|
| Free base unmilled | 10.5 | 4.0 | 8.8 |
| Tosylate milled | 2.4 | 1.3 | 3.4 |

Example 17 Oral Pharmocokinetic Study in Male Rats

Compound A (free base) and B (toslyate monohydrate salt of compound A) was administered to male rats, strain CD®, via oral gavage using 1% Poloxamer 407 or 0.5% carboxymethyl cellulose (CMC) as the vehicle (Table 1). All doses were calculated as free base equivalents.

TABLE 7

Experimental design

| Group | Test Article | Vehicle | Dose (mg/kg) | Number of Males |
|---|---|---|---|---|
| 1 | B | 1% Poloxamer 407 | 10 | 12 |
| 2 | B | 0.5% CMC | 10 | 12 |
| 3 | B | 0.5% CMC | 30 | 12 |
| 4 | B | 0.5% CMC | 75 | 12 |
| 5 | A | 1% Poloxamer 407 | 10 | 12 |
| 6 | A | 0.5% CMC | 10 | 12 |
| 7 | A | 0.5% CMC | 30 | 12 |
| 8 | A | 0.5% CMC | 75 | 12 |

For each dosing group blood was collected from 3 animals at each of the following time points: 0, 0.5, 1, 2, 4, 6, 8, 10, 12, 16, 24, and 48 hours post dose. Plasma was prepared using standard techniques with sodium heparin as anti-coagulant. The Compound A and B plasma concentrations were determined using a GLP-validated LC/MS/MS bioanalytical method. Pharmacokinetic analyses were performed using PK Solutions 2.0™ or WinNonLin 5.1.

The time-concentration profiles are shown in FIG. 15, and calculated pharmacokinetic parameters are shown in Table 8. From these data it is apparent that the tosylate monohydrate form (B) is consistently associated with greater values for Cmax and AUClast, irrespective of the vehicle, than the free base (A). For both these pharmacokinetic measures, the plasma levels were between 2 to 3 times higher for the tosylate monohydrate form than for the free base.

TABLE 8

Mean pharmacokinetic parameters for AFN-1252 following oral administration in male rats

| Dose (mg/kg) | Test Article | Vehicle | Cmax (ng/ml) | AUClast (hr*ng/ml) | Ratio of tosylate monohyrate/ free base Cmax | Ratio of tosylate monohyrate/ free base AUClast |
|---|---|---|---|---|---|---|
| 10 | AFN-12520000 | 0.5% CMC | 163 | 980 | | |
| | AFN-12520301 | 0.5% CMC | 347 | 2044 | 2.1 | 2.1 |
| | AFN-12520000 | 1% Poloxamer 407 | 157 | 883 | | |
| | AFN-12520301 | 1% Poloxamer 407 | 348 | 2663 | 2.2 | 3.0 |
| 30 | AFN-12520000 | 0.5% CMC | 176 | 1624 | | |
| | AFN-12520301 | 0.5% CMC | 434 | 3680 | 2.5 | 2.3 |
| 75 | AFN-12520000 | 0.5% CMC | 246 | 2373 | | |
| | AFN-12520301 | 0.5% CMC | 595 | 4256 | 2.4 | 1.8 |

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound of formula I:

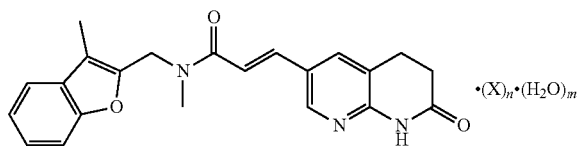

wherein
n is 1;
m is 0 or 1;
X is $HSO_3Ar$; and
Ar is aryl.

2. The compound of claim 1, wherein the compound is in a crystalline form.

3. The compound of claim 1, wherein n equals 1, m equals 1 and X is $HSO_3Ar$.

4. The compound of claim 1, wherein n equals 1, m equals 0 and X is $HSO_3Ar$.

5. The compound of claim 1, wherein the compound is an anhydrous p-toluenesulfonic salt.

Figure 13:
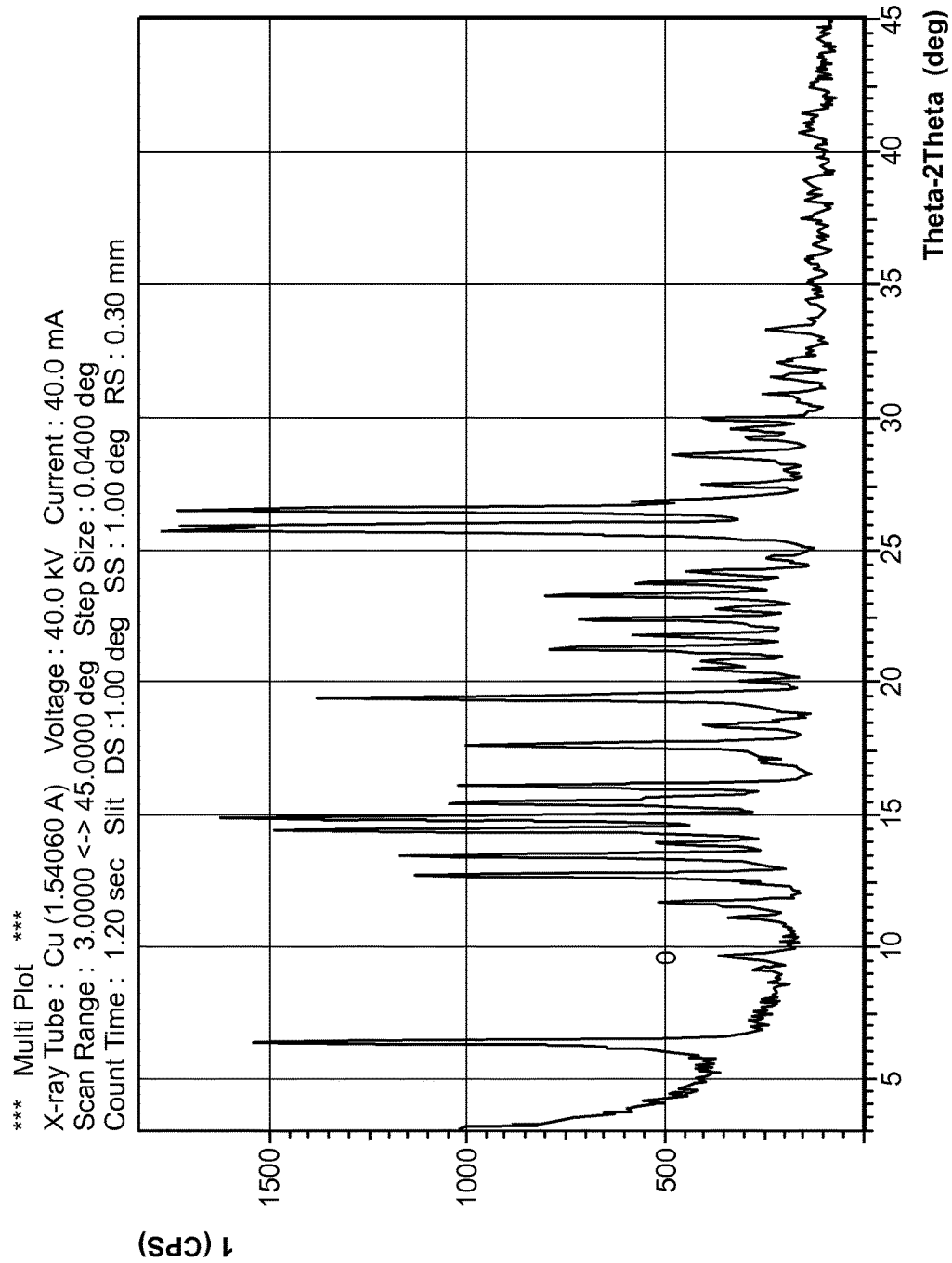
FIG. 13 depicts a XRPD spectra of the anhydrous form of p-toluenesulfonic salt of (E)-N-methyl-N-((3-methylbenzofuran-2-yl)methyl)-3-(7-oxo-5,6,7,8-tetrahydro-1,8-naphthyridin-3-yl)acrylamide.

6. The salt according to claim 5 with characteristic peaks in the powder X-ray diffraction pattern at values of 2θ as depicted in FIG. 13.

7. A composition comprising the compound of claim 1 and a pharmaceutically acceptable excipient.

8. A composition comprising (E)-N-methyl-N-((3-methylbenzofuran-2-yl)methyl)-3-(7-oxo-5,6,7,8-tetrahydro-1,8-naphthyridin-3-yl)acrylamide 4-methylbenzenesulfonate and a pharmaceutically acceptable excipient.

* * * * *